United States Patent

Lantzsch et al.

[11] Patent Number: 5,969,147
[45] Date of Patent: Oct. 19, 1999

[54] SUBSTITUTED BIPHENYLOXAZOLINES

[75] Inventors: Reinhard Lantzsch, Wuppertal; Albrecht Marhold, Leverkusen; Wolfgang Krämer, Burscheid; Christoph Erdelen, Leichlingen; Ulrike Wachendorff-Neumann, Bonn; Andreas Turberg, Erkrath; Norbert Mencke, Leverkusen, all of Germany

[73] Assignees: Bayer Aktiengesellschaft, Leverkusen, Germany; Yashima Chemical Industry Co., Ltd, Kanagawa, Japan

[21] Appl. No.: 09/191,850

[22] Filed: Nov. 12, 1998

Related U.S. Application Data

[62] Division of application No. 08/511,212, Aug. 4, 1995.

[30] Foreign Application Priority Data

Aug. 12, 1994 [DE] Germany ............... P 4428536
Dec. 12, 1994 [DE] Germany ............... P 4444108

[51] Int. Cl.[6] ............................. C07D 263/10
[52] U.S. Cl. ............... 548/237; 514/374; 514/340; 546/271.4; 564/256; 564/337; 568/642; 568/747; 568/746; 568/337
[58] Field of Search ........................ 548/237, 239

[56] References Cited

U.S. PATENT DOCUMENTS

| | | | |
|---|---|---|---|
| 3,901,906 | 8/1975 | Kozlik | 548/239 |
| 4,960,884 | 10/1990 | Roush et al. | 514/721 |
| 5,141,948 | 8/1992 | Miyamoto | 514/374 |
| 5,411,979 | 5/1995 | Hirose | 514/374 |
| 5,478,855 | 12/1995 | Suzuki et al. | 514/374 |
| 5,578,625 | 11/1996 | Suzuki et al. | 514/374 |
| 5,631,014 | 5/1997 | Ishida et al. | 514/374 |
| 5,686,393 | 11/1997 | Lahm et al. | 514/374 |
| 5,807,877 | 9/1998 | Lantzsch et al. | 514/374 |

FOREIGN PATENT DOCUMENTS

| | | |
|---|---|---|
| 0 432 661 | 6/1991 | European Pat. Off. . |
| 0 645 085 | 3/1995 | European Pat. Off. . |
| 0696584 | 8/1995 | European Pat. Off. . |
| WO 93/25079 | 12/1993 | WIPO . |
| WO 95/04726 | 2/1995 | WIPO . |
| WO 96/22283 | 7/1996 | WIPO . |
| WO 97-19067 | 5/1997 | WIPO . |

OTHER PUBLICATIONS

Suzuki et al., Synthesis, No. 5, pp. 499–500 (1985).
M. Kuroboshi et al., Synlett, vol. 4, pp. 251–252 (1994).

*Primary Examiner*—Donald G. Daus
*Attorney, Agent, or Firm*—Sprung Kramer Schaefer & Briscoe

[57] ABSTRACT

New pesticidal substituted biphenyloxazolines of the formula (I)

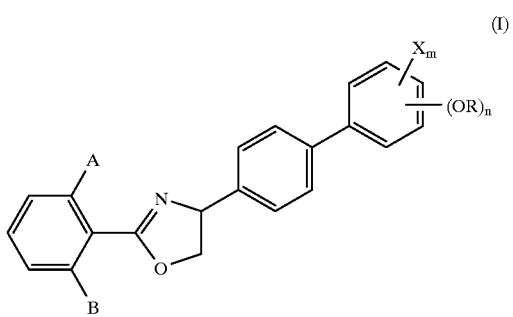

in which

A, B, X, m and n have the meanings stated in the description, and new intermediates therefor.

3 Claims, No Drawings

SUBSTITUTED BIPHENYLOXAZOLINES

This application is a divisional of application Ser. No. 08/511,212, filed on Aug. 4, 1995 (now pending).

SUBSTITUTED BIPHENYLOXAZOLINES

The invention relates to new substituted biphenyloxazolines, to a plurality of processes for their preparation, to new intermediates, and to the use of the substituted biphenyloxazolines for combating animal pests.

It is known that certain substituted biphenyloxazolines, such as 2-(2,6-difluorophenyl)-4-(4'-chlorobiphenyl-4)-2-oxazoline, have an insecticidal and acaricidal activity (cf. EP-A-0 432 661).

However, the level and/or duration of activity of these known compounds are not entirely satisfactory in all fields of application, in particular against certain organisms or when low concentrations are applied.

New substituted biphenyloxazolines of the formula (I)

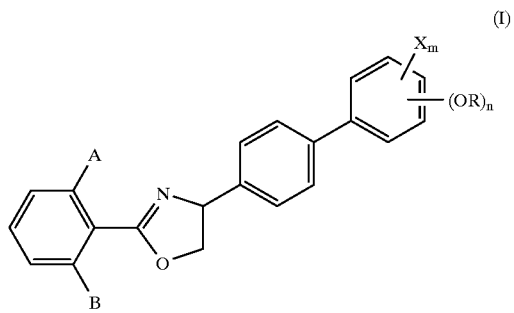

have been found,
in which
  A represents hydrogen, fluoro or chloro,
  B represents fluoro or chloro,
in which
  R represents $R^1$ or $R^2$, where
  $R^1$ represents halogenoalkyl or halogenocycloalkyl having in each case at least one fluorine atom and additionally at least one hydrogen or chlorine atom,
    or represents halogenocycloalkenyl having at least one fluorine atom,
  $R^2$ represents hydrogen, alkenyl, alkinyl, or represents optionally substituted cycloalkyl,
    or represents optionally substituted cycloalkylalkyl,
    or represents optionally substituted cycloalkenylalkyl,
    or represents optionally substituted cycloalkenyl,
    or represents phenylalkyl or naphthylalkyl, each of which is optionally substituted,
    or represents optionally substituted heteroarylalkyl,
    or represents the radical $COR^3$
in which
  $R^3$ represents alkyl, alkoxy, alkenyl, alkenyloxy,
    or represents cycloalkyl, cycloalkyloxy or cycloalkylalkyloxy, each of which is optionally substituted,
    or represents phenyl or naphthyl, each of which is optionally substituted,
    or represents the radical $NR^4R^5$,
in which
  $R^4$ represents hydrogen or alkyl and
  $R^5$ represents alkyl, halogenoalkyl, or represents cycloalkyl or cycloalkylalkyl, each of which is optionally substituted, or represents phenyl or phenylalkyl, each of which is optionally substituted,
  X represents halogen, alkyl or alkoxy,
  m represents 0, 1 or 2 and
  n represents 1 or 2.

Due to one or more chiral centers, the compounds of the formula (I) are generally obtained in the form of stereoisomer mixtures. They can be used in the form of their diastereomer mixtures and also as pure diastereomers or enantiomers.

Furthermore, it has been found that the new substituted biphenyloxazolines of the formula (I) are obtained by a process wherein A) in a first step, to obtain compounds of the formula (II)

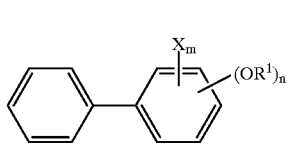

in which
  $R^1$, X, m and n have the abovementioned meanings,
  α) to obtain compounds of the formula (IIa)

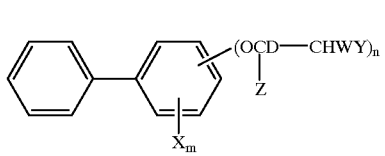

in which
  W and Y independently of one another represent fluorine, chlorine or trifluoromethyl,
  D represents hydrogen or fluorine,
  Z represents fluorine or
  W and Z together represent $-(CF_2)_l$
in which
  l represents 2, 3 or 4,
  n represents 1 or 2 and
  m represents 0, 1 or 2,
a hydroxybiphenyl of the formula (III)

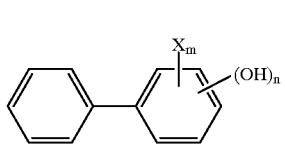

in which
  X, m and n have the abovementioned meanings,
is reacted with a compound of the formula (IV)

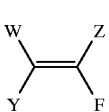

in which
  W, Y and Z have the abovementioned meanings, if appropriate in the presence of a base, if appropriate in the presence of a catalyst and if appropriate in the presence of a diluent and, if appropriate, the product is subsequently hydrogenated, or β) to obtain compounds of the formula (IIb)

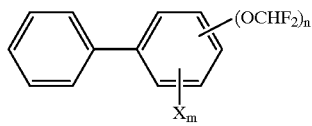
(IIb)

in which

X, m and n have the abovementioned meanings,
hydroxybiphenyls of the abovementioned formula (III) are reacted with a difluorohalogenomethane of the formula (V)

 (V)

in which

Hal represents chlorine or bromine, if appropriate in the presence of a base, if appropriate in the presence of a catalyst and if appropriate in the presence of a diluent, or γ) to obtain compounds of the formula (IIc)

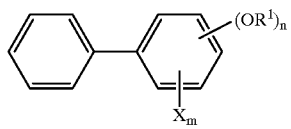
(IIc)

in which

X, $R^1$, m and n have the abovementioned meanings,
aminophenol derivatives of the formula (VI)

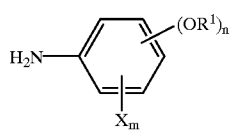
(VI)

in which

X, $R^1$, m and n have the abovementioned meanings,
are diazotized and the resulting diazonium salt is reacted with benzene in the presence of acid and iron powder or in the presence of a base and in each case, if appropriate, in the presence of a diluent, or δ) to obtain compounds of the formula (IId)

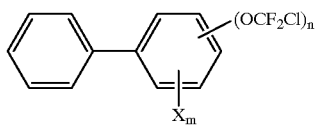
(IId)

in which

X, m and n have the abovementioned meanings,
a hydroxybiphenyl of the abovementioned formula (III) is reacted with carbon tetrachloride in the presence of hydrofluoric acid, if appropriate in the presence of a diluent, B) in a second step, to obtain compounds of the formula (VII)

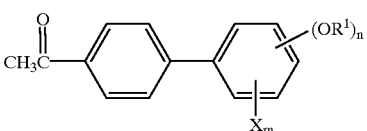
(VII)

in which

X, $R^1$, m and n have the abovementioned meanings,

α) the compounds of the formula (II) which can be obtained by process A) are reacted with acetyl chloride in the presence of an acid or Lewis acid and in the presence of a diluent, or β) to obtain compounds of the formula (VIIa)

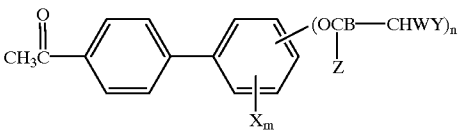
(VIIa)

in which

B, X, m, n, W, Y and Z have the abovementioned meanings,
a hydroxybiphenyl derivative of the formula (IIa)

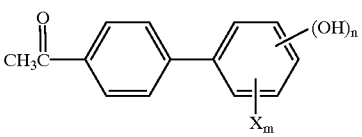
(IIIa)

in which m and n have the abovementioned meanings, is reacted with a compound of the formula (IV)

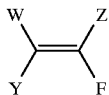
(IV)

in which

W, Y and Z have the abovementioned meanings, if appropriate in the presence of a base, if appropriate in the presence of a catalyst and if appropriate in the presence of a solvent and, if appropriate, the product is subsequently hydrogenated, or γ) to obtain compounds of the formula (VIIb)

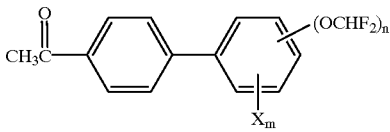
(VIIb)

in which

X, m and n have the abovementioned meanings, a hydroxybiphenyl derivative of the formula (IIIa) shown above is reacted with a difluorohalogenomethane of the formula (V) shown above, if appropriate in the presence of a base, if appropriate in the presence of a catalyst and if appropriate in the presence of a diluent, C) in a third step, to obtain compounds of the formula (VIII)

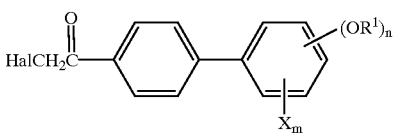
(VIII)

in which

X, $R^1$, m and n have the abovementioned meanings and

Hal represents chlorine or bromine,

α) the compounds of the formula (VII) shown above, which can be obtained by process B), are chlorinated or brominated, if appropriate in the presence of a diluent, or β) the compounds of the formula (11) shown above, which can be obtained by process A), are reacted with halogenoacetyl chlorides of the formula (IX)

  HalCH$_2$COCl  (IX)

in which

Hal represents chlorine or bromine, in the presence of an acid or Lewis acid and in the presence of a diluent, D) in a fourth step, to obtain compounds of the formula (X)

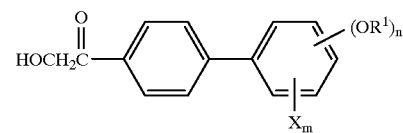
(X)

in which

X, $R^1$, m and n have the abovementioned meanings, the compounds of the formula (VIII) shown above, which can be obtained by process C), are reacted with a salt of formic acid, in the presence of a diluent and if appropriate in the presence of a catalyst, E) in a fifth step, to obtain compounds of the formula (XI)

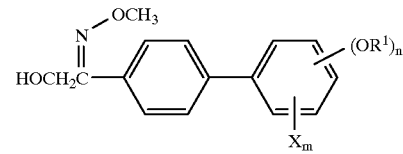
(XI)

in which

X, $R^1$, m and n have the abovementioned meanings, the compounds of the formula (X) shown above, which can be obtained by process D), are reacted with the compound of the formula (XII)

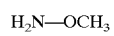  H$_2$N—OCH$_3$  (XII), if appropriate in the presence of a diluent,

F) in a sixth step, to obtain compounds of the formula (XIII)

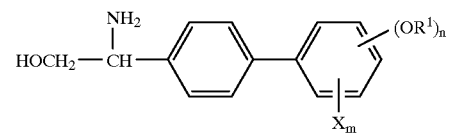
(XIII)

in which $R^1$, X, m and n have the abovementioned meanings, the compounds of the formula (XI) shown above, which can be obtained by process E), are reduced using a reducing agent in the presence of an acid and if appropriate in the presence of a diluent, G) in a seventh step, to obtain compounds of the formula (XIV)

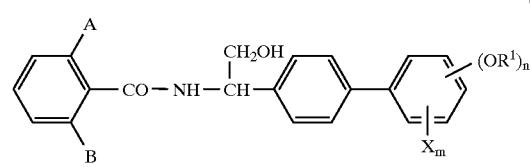
(X)

in which

A, B, $R^1$, X, m, and n have the abovementioned meanings, either

α) the compounds of the formula (MII) shown above, which can be obtained by process F), are reacted with 2-A, 6-B- benzoyl chloride if appropriate in the presence of a base and if appropriate in the presence of a diluent, or β) the compounds of the formula (II) shown above, which can be obtained by process A), are first reacted with a compound of the formula (XV)

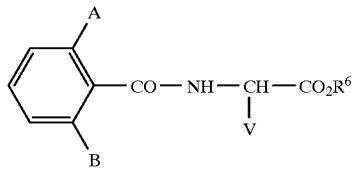
(XV)

in which

A and B have the abovementioned meanings,

V represents chlorine, hydroxyl or $C_1$–$C_4$-alkoxy and $R^6$ represents hydrogen or alkyl, preferably hydrogen or $C_1$–$C_6$-alkyl, in the presence of an acidic catalyst and if appropriate in the presence of a diluent, and the resulting compounds of the formula (XVI)

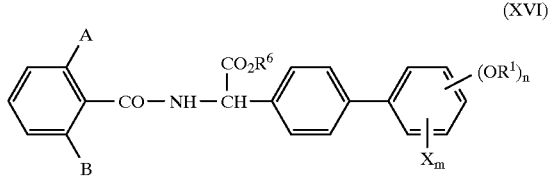
(XVI)

in which

A, B, $R^1$, X, m, n and $R^6$ have the abovementioned meanings, are reduced by means of a reducing agent in the presence of a diluent, H) in an eighth step, to obtain compounds of the formula (XVII)

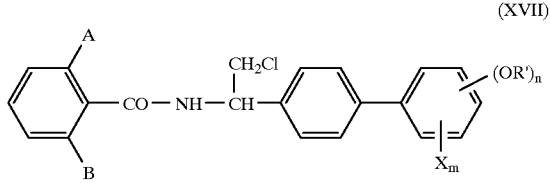
(XVII)

in which

A, B, X, m and n have the abovementioned meanings,

R' represents $R^1$ or $COR^3$, in which
$R^1$ and $R^3$ have the abovementioned meanings either α) the compounds of the formula (XIV) shown above, which can be obtained by process G), are reacted with a chlorinating agent, if appropriate in the presence of a diluent, or β) the compounds of the formula (II) shown above, which can be obtained by process A), or a compound of the formula (IIe)

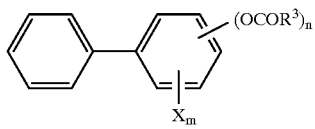
(IIe)

in which $R^3$, X, n and m have the abovementioned meanings, are reacted with a compound of the formula (XVIII)

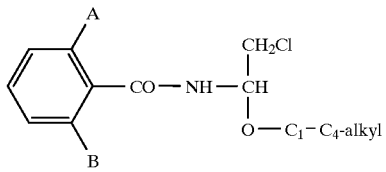
(XVIII)

in the presence of an acidic catalyst and if appropriate in the presence of a diluent, and I) in a ninth step, the compounds of the formula (XVII) shown above, which can be obtained by process H), are cyclized in the presence of a base, if appropriate in the presence of a catalyst and if appropriate in the presence of a diluent, and, if appropriate, J) the compounds of the formula (Ia) obtained for $R=COR^3$

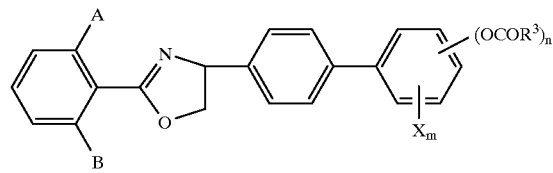
(Ia)

in which

A, B, $R^3$, X, n and m have the abovementioned meanings, are hydrolysed to give compounds of the formula (Ib)

(Ib)

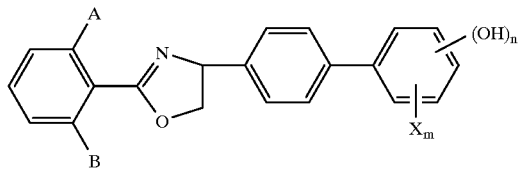
(Ib)

in which

A, B, X n and m have the abovementioned meanings and, if appropriate, these are subsequently Kα) reacted with a compound of the formula (XIX)

HalCOR³ (XIX)

in which $R^3$ has the abovementioned meaning and

Hal represents halogen, preferably chlorine or bromine, if appropriate in the presence of a diluent and if appropriate in the presence of a base, or β) reacted with a compound of the formula (IV)

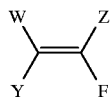
(IV)

in which

W, Y and Z have the abovementioned meanings, if appropriate in the presence of a base, if appropriate in the presence of a catalyst and if appropriate in the presence of a diluent, and, if appropriate, the product is subsequently hydrogenated, or γ) reacted with a difluorohalogenomethane of the formula (V $$CHF_2Hal \quad (V)$$

in which

Hal represents chlorine or bromine, if appropriate in the presence of a base, if appropriate in the presence of a catalyst and if appropriate in the presence of a diluent, or δ) reacted with carbon tetrachloride in the presence of hydrofluoric acid, if appropriate in the presence of a diluent, or ε) reacted with a compound of the formula (XX)

$$M—R^2 \quad (XX)$$

in which $R^2$ has the abovementioned meaning and

M represents a leaving group, if appropriate in the presence of a diluent and if appropriate in the presence of a base.

Furthermore, it has been found that the new substituted biphenyloxazolines of the formula (I) are highly suitable for combating animal pests, in particular insects, arachnids and nematodes which occur in agriculture, in afforestations, in the protection of stored products and of materials and in the hygiene field.

Formula (I) provides a general definition of the compounds according to the invention.

Preferred substituents or ranges of the radicals listed in the formulae mentioned hereinabove and hereinbelow are explained below.

A represents hydrogen, fluoro or chloro,

B represents fluoro or chloro,

R preferably represents $R^1$ or $R^2$, where $R^1$ represents $C_1$–$C_6$-halogenoalkyl or $C_3$–$C_6$-halogenocycloalkyl having in each case at least one fluorine atom and additionally at least one hydrogen or chlorine atom, or represents $C_4$-$C_6$-halogenocycloalkenyl having at least one fluorine atom and $R^2$ represents hydrogen, $C_3$–$C_{12}$-alkenyl, $C_3$–$C_{12}$-alkinyl, or represents $C_3$–$C_6$-cycloalkyl which is optionally substituted by $C_1$–$C_4$-alkyl, $C_2$–$C_4$-alkenyl, $C_2$–$C_4$-halogenoalkenyl, phenyl, halogenophenyl, styryl or halogenostyryl, or represents $C_3$–$C_6$-cycloalkyl-$C_1$–$C_4$-alkyl which is optionally substituted by halogen, $C_1$–$C_4$-alkyl, $C_2$–$C_4$-alkenyl, $C_2$–$C_4$-halogenoalkenyl, phenyl, halogenophenyl, styryl or halogenostyryl, or represents $C_4$–$C_6$-cycloalkenyl-$C_1$–$C_4$-alkyl which is optionally substituted by halogen or $C_1$–$C_4$-alkyl, or represents $C_4$–$C_6$-cycloalkenyl which is optionally substituted by $C_1$–$C_4$-alkyl, or represents phenyl-$C_1$–$C_6$-alkyl, naphthyl-$C_1$–$C_3$-alkyl or tetrahydronaphthyl-$C_1$–$C_3$-alkyl, each of which is optionally monosubstituted to tetrasubstituted by identical or different substituents from the series consisting of nitro, halogen, $C_1$–$C_{12}$-alkyl, $C_1$–$C_{12}$-halogenoalkyl, $C_1$–$C_{12}$-alkoxy or $C_1$–$C_{12}$-halogenoalkoxy, or represents 5- or 6-membered heteroaryl-$C_1$–$C_4$-alkyl which is optionally monosubstituted or disubstituted by identical or different substituents from the series consisting of nitro, halogen, $C_1$–$C_{12}$-alkyl, $C_1$–$C_{12}$-halogenoalkyl, $C_1$–$C_{12}$-alkoxy or $C_1$–$C_{12}$-halogenoalkoxy and which has 1 or 2 identical or different hetero atoms from the series consisting of nitrogen, oxygen and sulfur, or represents the radical $COR^3$.

$R^3$ preferably represents $C_1$–$C_{12}$-alkyl, $C_1$–$C_2$-alkoxy, $C_3$–$C_{12}$-alkenyl, $C_3$–$C_{12}$-alkenyloxy, or represents $C_3$–$C_{10}$-cycloalkyl, $C_3$–$C_{10}$-cycloalkyloxy or $C_3$–$C_{10}$-cycloalkyl-$C_1$–$C_6$-alkyloxy, each of which is optionally substituted by halogen, $C_1$–$C_4$-alkyl, $C_1$–$C_4$-halogenoalkyl, $C_2$–$C_4$-alkenyl or $C_2$–$C_4$-halogenoalkenyl, or represents phenyl or naphthyl, each of which is optionally monosubstituted to tetrasubstituted by identical or different substituents from the series consisting of halogen, $C_1$–$C_{12}$-alkyl, $C_1$–$C_{12}$-halogenoalkyl, $C_1$–$C_{12}$-alkoxy or $C_1$–$C_{12}$-halogenoalkoxy, or represents the radical $NR^4R^5$.

$R^4$ preferably represents hydrogen or $C_1$–$C_{12}$-alkyl.

$R^5$ preferably represents $C_1$–$C_{12}$-alkyl, $C_1$–$C_{12}$-halogenoalkyl, or represents $C_3$–$C_{10}$-cycloalkyl or $C_3$–$C_{10}$-cycloalkyl-$C_1$–$C_6$-alkyl, each of which is optionally substituted by halogen, $C_1$–$C_4$-alkyl, $C_1$–$C_4$-halogenoalkyl or $C_2$–$C_4$-halogenoalkenyl, of represents phenyl or phenyl-$C_1$–$C_6$-alkyl, each of which is optionally monosubstituted to tetrasubstituted by identical or different substituents from the series consisting of halogen, $C_1$–$C_{12}$-alkyl, $C_1$–$C_{12}$-halogenoalkyl, $C_1$–$C_{12}$-alkoxy, $C_1$–$C_{12}$-halogenoalkoxy.

X preferably represents halogen, $C_1$–$C_6$-alkyl or $C_1$–$C_{12}$-alkoxy.

m preferably represents 0, 1 or 2.

n preferably represents 1 or 2.

A particularly preferably represents hydrogen, fluoro or chloro,

B particularly preferably represents fluoro or chloro,

R particularly preferably represents $R^1$ or $R^2$, where $R^1$ represents $C_1$–$C_3$-halogenoalkyl or $C_4$–$C_5$-halogenocycloalkyl having in each case at least one fluorine atom and additionally at least one hydrogen or chlorine atom, or represents $C_4$–$C_6$-halogenocycloalkenyl having at least one fluorine atom and $R^2$ represents hydrogen, $C_3$–$C_{12}$-alkenyl, $C_3$–$C_5$-alkinyl, or represents $C_3$–$C_6$-cycloalkyl which is optionally substituted by $C_1$–$C_4$-alkyl, $C_2$–$C_4$-alkenyl, $C_2$–$C_3$- halogenoalkenyl, phenyl, halogenophenyl, styryl or halogenostyryl, or represents $C_3$–$C_6$-cycloalkyl-$C_1$–$C_4$-alkyl, which is optionally substituted by halogen, $C_1$–$C_4$-alkyl, $C_{21}$–$C_4$-alkenyl, $C_2$–$C_3$-halogenoalkenyl, phenyl, halogenophenyl, styryl or halogenostyryl, or represents $C_4$–$C_6$-cycloalkenylmethyl which is optionally substituted -by halogen, or represents $C_4$–$C_6$-cycloalkenyl, or represents phenyl-$C_1$–$C_6$-alkyl, naphthylmethyl, tetrahydronaphthylmethyl, pyridyl-, furanyl-, thiazolyl-, oxazolyl- or isoxazolyl-$C_1$–$C_3$-alkyl, each of which is optionally monosubstituted or disubstituted by identical or different substituents from the series consisting of nitro, halogen, $C_1$–$C_4$-alkyl, $C_1$–$C_4$-halogenoalkyl, $C_1$–$C_4$-alkoxy or $C_1$–$C_4$-halogenoalkoxy, or represents the radical $COR^3$.

$R^3$ particularly preferably represents $C_1$–$C_6$-alkyl, $C_1$–$C_6$-alkoxy, $C_3$–$C_6$-alkenyl, $C_3$–$C_6$-alkenyloxy, or represents $C_3$–$C_6$-cycloalkyl, $C_3$–$C_6$-cycloalkyloxy or $C_3$–$C_6$-cycloalkyl-$C_1$–$C_2$-alkyloxy, each of which is optionally substituted by fluorine, chlorine, $C_1$–$C_3$-alkyl, $C_1$–$C_2$-halogenoalkyl or $C_2$–$C_3$-halogenoalkenyl or represents phenyl which is optionally monosubstituted or disubstituted by identical or different substituents from the series consisting of halogen, $C_1$–$C_4$-alkyl, $C_1$–$C_3$-halogenoalkyl, $C_1$–$C_4$-alkoxy or $C_1$–$C_4$-halogenoalkoxy, or represents the radical NHR.

$R^5$ particularly preferably represents $C_1$–$C_4$-alkyl, phenyl or benzyl each of which is optionally monosubstituted or disubstituted by identical or different substituents from the series consisting of fluorine, chlorine, bromine, $C_1$–$C_4$-alkyl, $C_1$–$C_4$-halogenoalkyl or $C_1$–$C_4$-halogenoalkoxy.

X particularly preferably represents fluorine, chlorine or bromine.

m particularly preferably represents 0 or 1.

n particularly preferably represents 1.

A very particularly preferably represents hydrogen, fluoro or chloro,

B very particularly preferably represents fluoro or chloro,

R very particularly preferably represents $R^1$ or $R^2$, where $R^1$ represents one of the groups —$CHF_2$, —$CClF_2$, —$CF_2CFFCl$, —$CF_2CH_2F$, —$CF_2CHF_2$, —$CF_2CCl_3$, —$CF_2CHFCF_3$, —$CH_2CF_3$, —$CH_2CF_2CHF_2$, —$CH_2CF_2CF_3$,

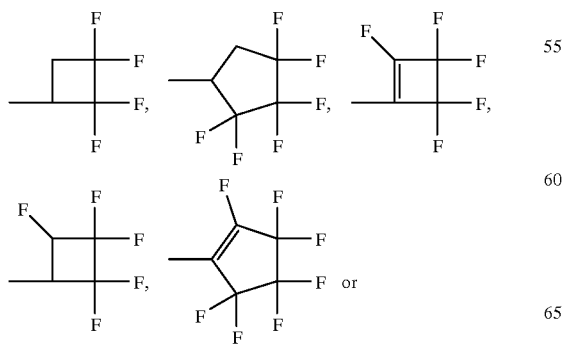

-continued

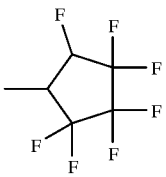

$R^2$ represents hydrogen, or represents propenyl, butenyl, pentenyl, hexenyl, propinyl, butinyl, pentinyl, or represents one of the cycloalkylalkyl groups:

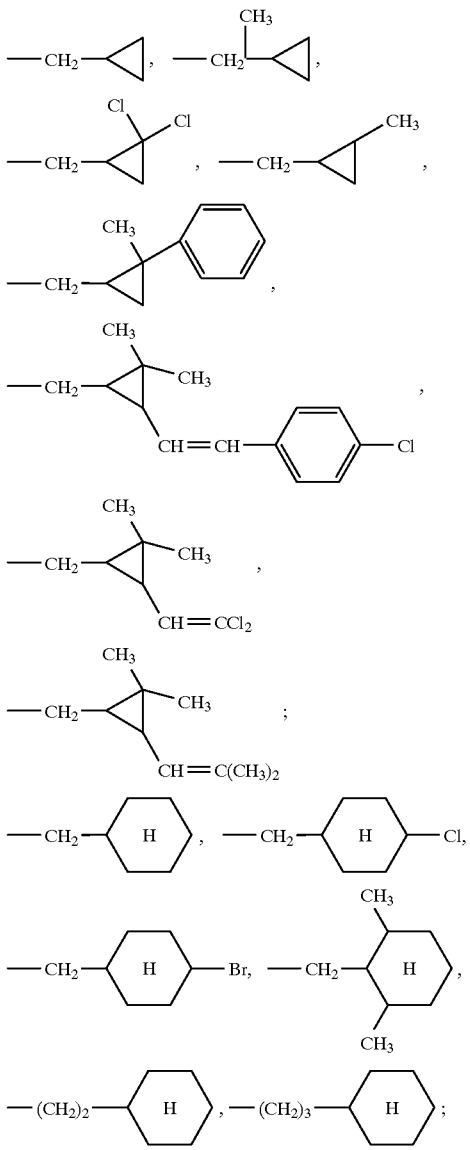

or represents the cycloalkenylalkyl group:

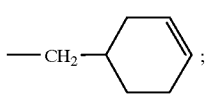

or represents one of the phenylalkyl groups:

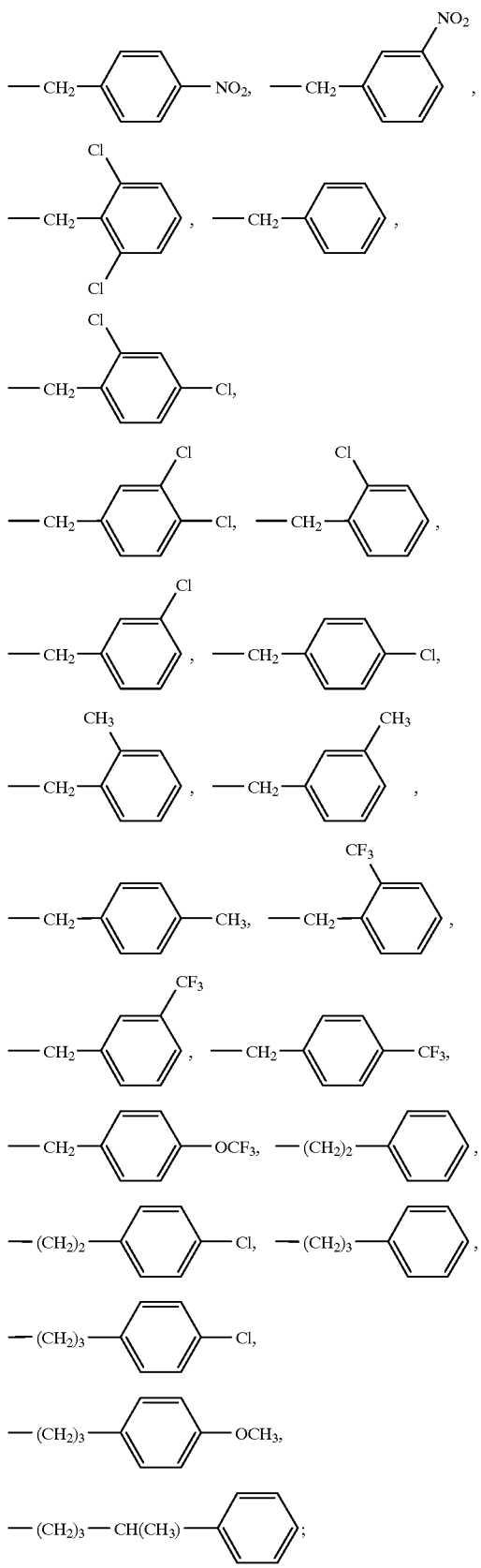

or represents

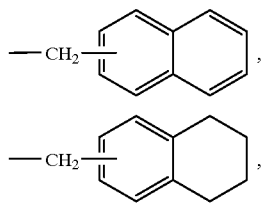

or represents one of the heteroarylalkyl groups:

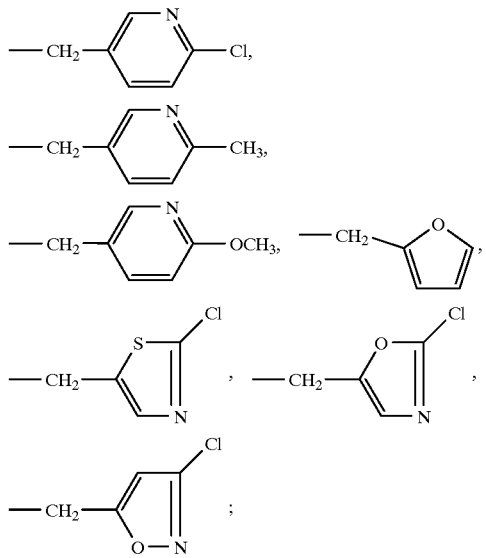

or represents the radical —COR$^3$.

R$^3$ very particularly preferably represents methyl, ethyl, propyl;
or represents methoxy, ethoxy, propoxy, butoxy;
or represents cyclopropyl, cyclohexyl;
or represents cyclohexyloxy;
or represents phenyl, 2-chlorophenyl, 3-chlorophenyl, 2,6-difluorophenyl, 2-trifluoromethoxyphenyl, 4-trifluoromethoxyphenyl; 2,4-dichlorophenyl; 3,4-dichlorophenyl;
or represents the radical —NHR$^5$.

R$^5$ very particularly preferably represents methyl, ethyl, or represents phenyl which is optionally monosubstituted by chlorine.

X very particularly preferably represents fluorine, chlorine or bromine.

m very particularly preferably represents 0 or 1.

n very particularly preferably represents 1.

Other preferred compounds are those of the formula (Ic)

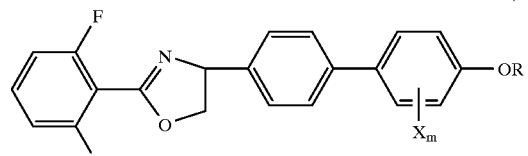

(Ic)

in which

R, X and m have the abovementioned general, preferred, particularly preferred or very particularly preferred meanings.

Other preferred compounds are those of the formula (Id)

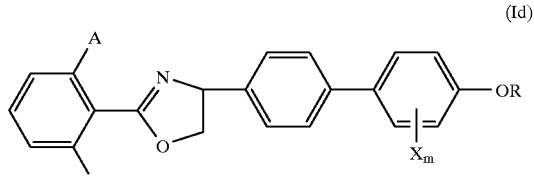

(Id)

in which

A represents hydrogen, B represents fluoro and R, X and m have the abovementioned general, preferred, particularly preferred or very particularly preferred meanings.

Other preferred compounds are those of the abovementioned formula (Id), in which A represents hydrogen, B represents chloro and R, X and m have the abovementioned general, preferred, particularly preferred or very particularly preferred meanings.

The hydrocarbon radicals, such as alkyl or alkenyl, which have been mentioned above in in the definition of the compounds according to the invention, also in connection with hetero atoms such as alkoxy, are, as far as possible, in each case straight-chain or branched.

The abovementioned definitions of radicals or explanations, in general or where preferred ranges have been mentioned, can be combined with each other as desired, that is to say that combinations between the respective ranges and preferred ranges are also possible. They apply analogously to the end products and to the precursors and intermediates.

Preferred according to the invention are those compounds of the formula (I) in which the meanings mentioned above as being preferred (preferable) are combined.

Particularly preferred according to the invention are those compounds of the formula (I) in which the meanings mentioned above as being particularly preferred are combined.

Very particularly preferred according to the invention are those compounds of the formula (I) in which the meanings mentioned above as being very particularly preferred are combined.

If, for example, 4-hydroxybiphenyl and trifluorochloroethylene are used as starting substances in accordance with process Aα), the course of the process according to the invention can be represented by the following equation:

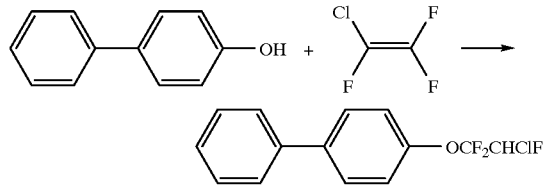

If, for example, 4-hydroxybiphenyl and difluorobromomethane are used as starting substances in accordance with process Aβ), the course of the process according to the invention can be represented by the following equation:

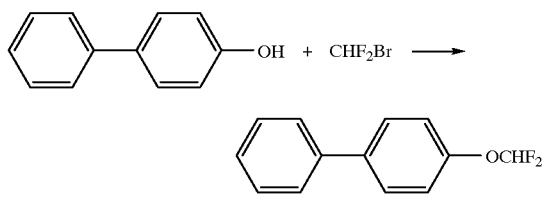

If, for example, 4-difluoromethoxyaniline is used as starting substance in accordance with process Aγ), the course of the process according to the invention can be represented by the following equation:

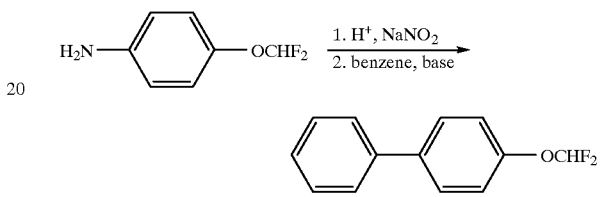

If, for example, 4-hydroxybiphenyl is used as starting substance in accordance with process Aδ), the course of the process according to the invention can be represented by the following equation:

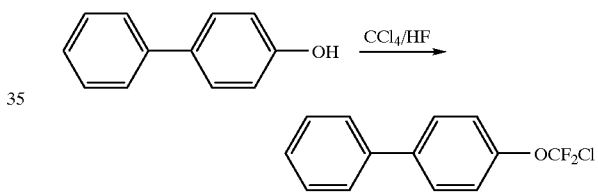

If, for example, 4-difluorochloromethoxybiphenyl is used as starting substance in accordance with process Bα), the course of the process according to the invention can be represented by the following equation:

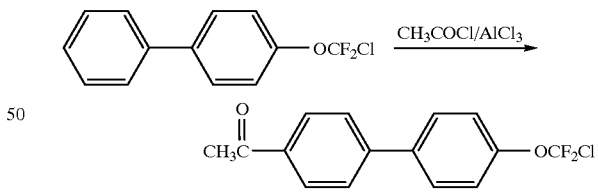

If, for example, 4-acetyl-4'-hydroxybiphenyl and hexafluorocyclobutene are used as starting substances in accordance with process Bβ), the course of the process according to the invention can be represented by the following equation:

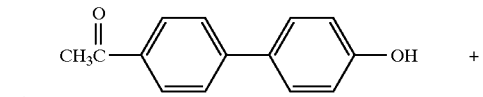

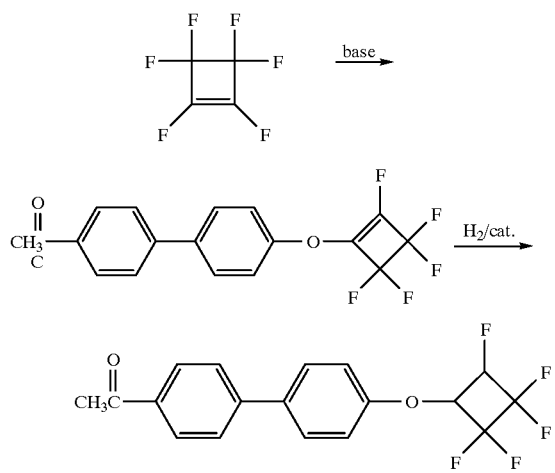

If, for example, 4-acetyl-4'-hydroxybiphenyl and chlorodifluoromethane are used as starting substances in accordance with process Bγ), the course of the process according to the invention can be represented by the following equation:

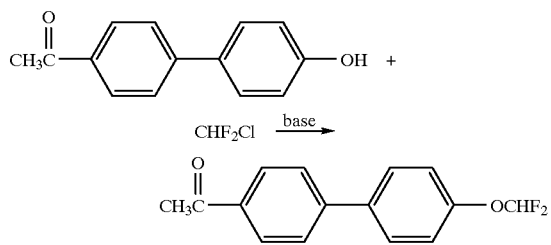

If, for example, 4-acetyl-4'-difluoromethoxybiphenyl is used as starting substance in accordance with process Cα), the course of the process according to the invention can be represented by the following equation:

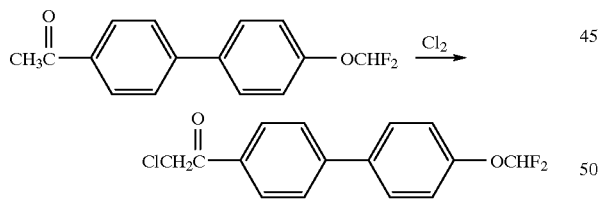

If, for example, 4-difluorochloromethoxybiphenyl and chloroacetyl chloride are used as starting substances in accordance with process Cβ), the course of the process according to the invention can be represented by the following equation:

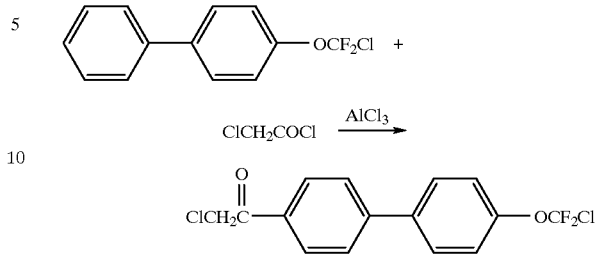

If, for example, 4-chloroacetyl-4'-difluoromethoxybiphenyl is used as starting substance in accordance with process D), the course of the process according to the invention can be represented by the following equation:

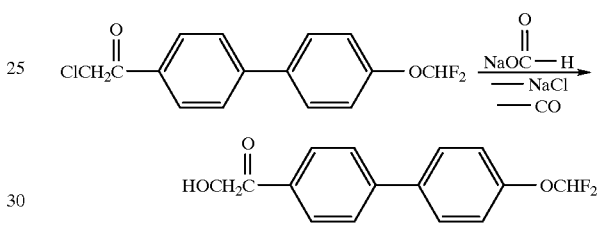

If, for example, 4-hydroxyacetyl-4'-difluorochloromethoxybiphenyl is used as starting substance in accordance with process E), the course of the process according to the invention can be represented by the following equation:

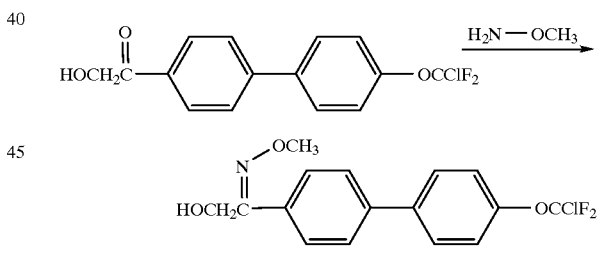

If, for example, 4-hydroxyacetyl-oxime 0-methyl ether 4'-trifluorochloroethoxy-10 biphenyl is used as starting substance in accordance with process F), the course of the process according to the invention can be represented by the following equation:

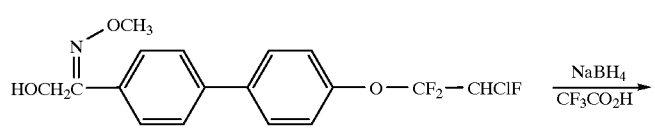

-continued

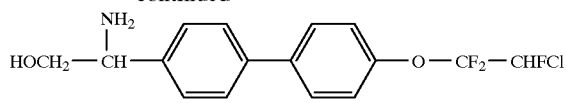

If, for example, 2-amino-2-(4-difluorochloromethoxybiphenyl)-4)-ethan-1-ol is used as starting material in accordance with process Gα), the course of the process according to the invention can be represented by the following equation:

If, for example, N-(1-(4'-difluoromethoxybiphenyl-4)-ethyl-2-ol)-2,6-difluorobenzamide and thionyl chloride are used as starting substances in accordance with process Hα), the course of the process according to the invention can be represented by the following equation:

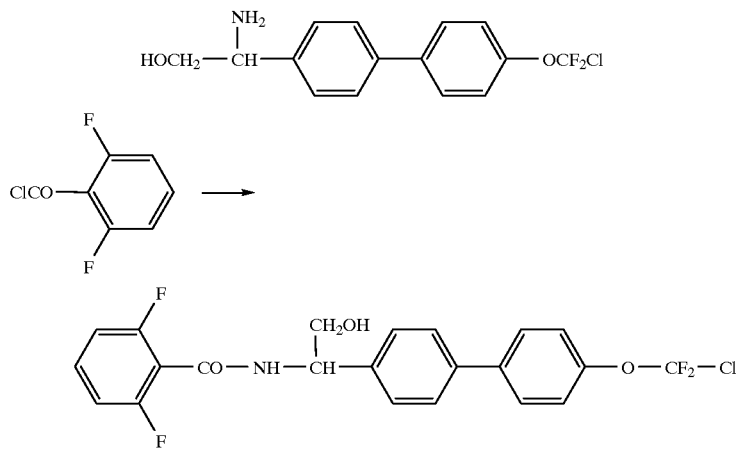

If, for example, N-(carboxymethylchloromethyl)-2,6-difluorobenzamide and 4-difluorochloromethoxybiphenyl are used as starting substances in accordance with process Gβ), the course of the process according to the invention can be represented by the following equation:

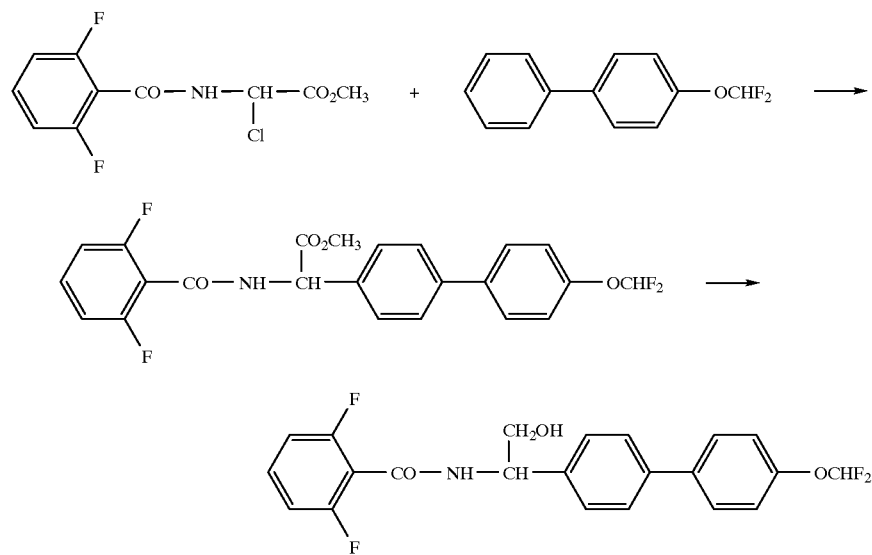

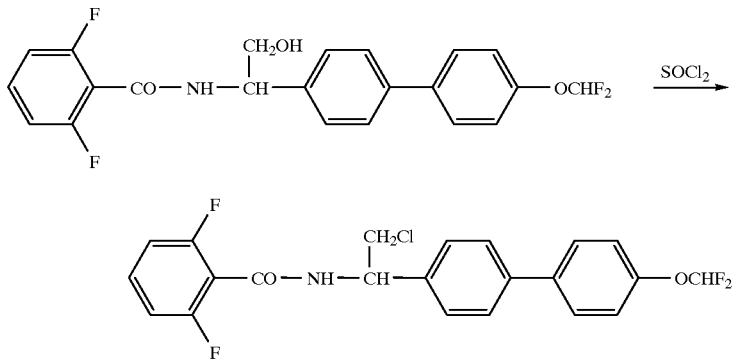

If, for example, N-1-methoxy-2-chloroethyl)-2,6-difluorobenzamide and 4-difluoromethoxybiphenyl are used as starting substances in accordance with process Hβ), the course of the process according to the invention can be represented by the following equation:

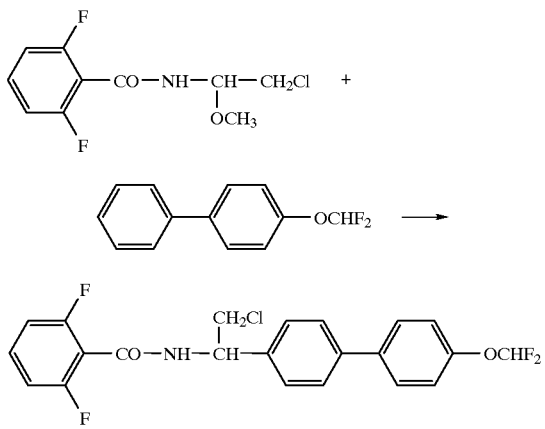

If, for example, N-(1-(4'-difluoromethoxybiphenyl-4-)2-chloroethyl)-2,6-difluorobenzarnide is used as starting substance in accordance with process I), the course of the process according to the invention can be represented by the following equation

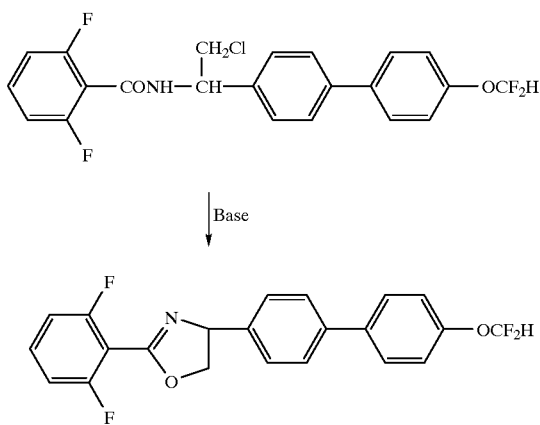

If, for example, 2-(2,6-difluorophenyl)-4-(4'-tert-butylcarbonyloxybiphenyl-4)-2-oxazoline is used as starting compound in accordance with process J), the course of the process according to the invention can be represented by the following equation:

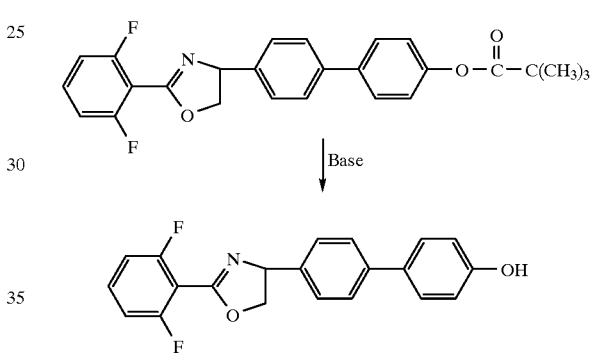

If, for example, 2-(2,6-difluorophenyl)-4-(4'-hydroxybiphenyl-4)-2-oxazoline and ethyl chloroformate are used as starting compounds in accordance with the process Kα), the course of the process according to the invention can be represented by the following equation:

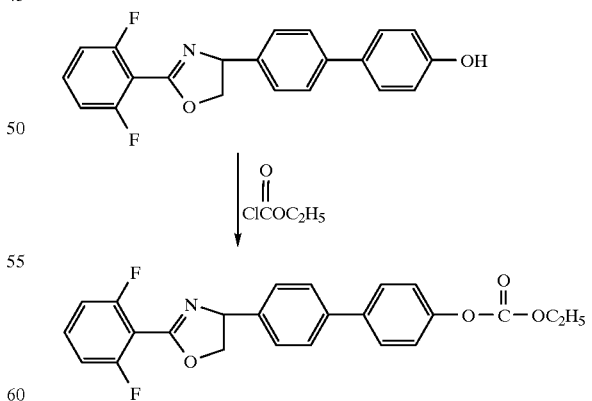

If, for example, 2-(2,6-difluorophenyl)-4-(4'-hydroxybiphenyl-4)-2-oxazoline, and trifluorochloroethylene are used as starting substances in accordance with process Kβ), the course of the process according to the invention can be represented by the following equation:

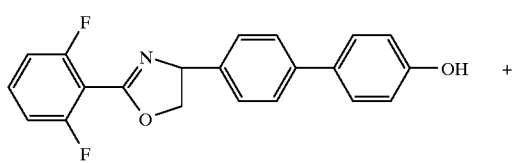

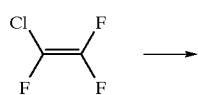

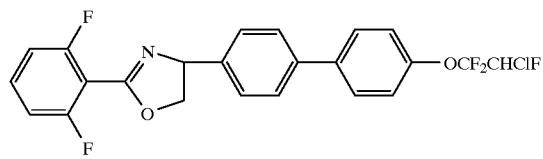

If, for example, 2-(2,6-difluorophenyl)-4-(4'-hydroxybiphenyl-4)-2-oxazoline and difluorochloromethane are used as starting substances in accordance with Example Kγ), the course of the process according to the invention can be represented by the following equation:

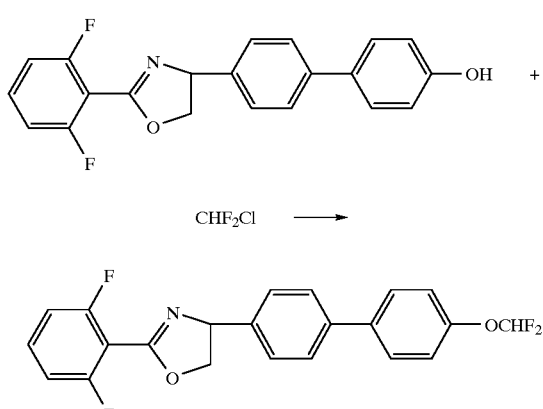

If, for example, 2-(2,6-difluorophenyl)-4-(4'-hydroxybiphenyl-4)-2-oxazoline and carbon tetrachloride are used as starting substances in accordance with Example Kδ), the course of the process according to the invention can be represented by the following equation:

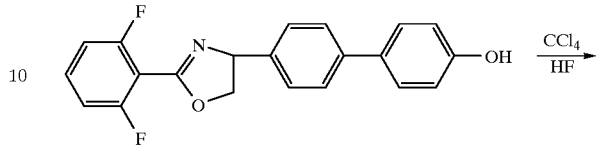

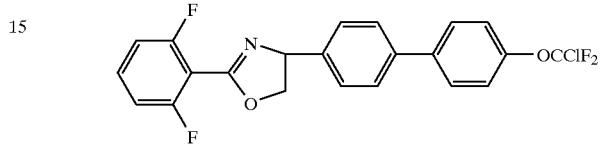

If, for example, 2-(2,6-difluorophenyl)-4-(4'-hydroxybiphenyl-4)-2-oxazoline and allyl bromide are used as starting substances in accordance with Example Kε), the course of the process according to the invention can be represented by the following equation:

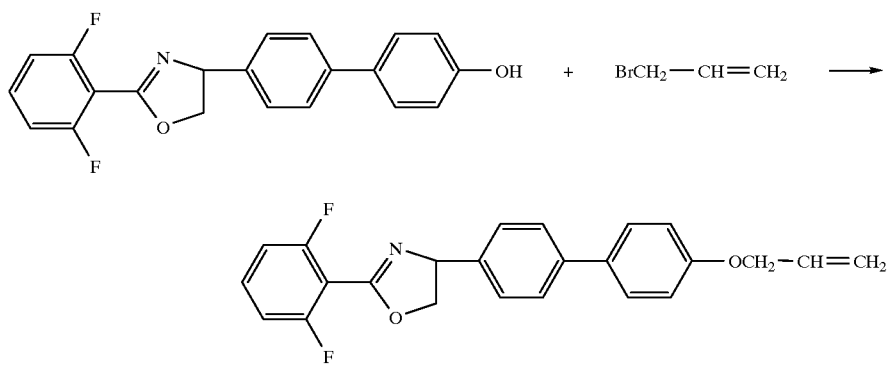

The compounds of the formula (III), which are required as starting substances for carrying out process Aα) according to the invention, are known and/or can be prepared in a simple manner by known methods.

For example, the compounds of the formula (III) are obtained by sulfonating optionally substituted biphenyls and then reacting the product with alkali metal hydroxides to give the hydroxybiphenyls, or by diazotizing aminobiphenyls and boiling the product (cf., for example, Houben-Weyl, Volume VI/1c (1976), pages 216 and 251).

The compounds of the formula (IV) which are furthermore required as starting substances for carrying out the processes Aα), Bβ) and Kβ) according to the invention are known and/or can be prepared in a simple manner by known methods (cf., for example, Houben-Weyl, Volume V/3 (1962), page 187 et seq., 317, 346 et seq. and 377 et seq.)

The difluorohalogenomethanes of the formula (V) which are required as starting substances for carrying out the processes Aβ) and Kγ) according to the invention are generally known compounds of organic chemistry.

The compounds of the formula (VI) which are required as starting substances for carrying out process Aγ) according to the invention are known and/or can be prepared in a simple manner by known methods.

The compounds of the formula (VI) are obtained for example by reducing the corresponding nitroaromatics or by subjecting the corresponding carboxamides e.g. to a Hofmann degradation.

The halogenoacetyl chlorides of the formula (IX) which are required as starting substances for carrying out process Cβ) according to the invention are conventional, generally known chemicals of organic chemistry.

The compound (XII) which is required for carrying out process E) according to the invention is a generally known chemical of organic chemistry.

The compounds of the formula (XV) which are required as starting substances for carrying out process Gβ) according to the invention are known and/or can be prepared in a simple manner by known methods (cf., for example, WO 93/24 470).

The compounds of the formula (XVIII) which are required as starting substances for carrying out process Hβ) according to the invention are known and/or can be prepared in a simple manner by known methods (cf., for example, EP-A-0 594 179). The compounds of the formula (IIe) which are also required as starting substances for carrying out process Hβ) according to the invention are known and/or can be obtained in a simple manner, for example by acylating the corresponding hydroxybiphenyls.

The compounds of the formula (XIX) which are required as starting substances for carrying out process Kα) according to the invention are generally known compounds of organic chemistry.

The compounds of the formula (XX) which are required as starting substances for carrying out process Kε) according to the invention are generally known compounds of organic chemistry.

M represents a customary leaving group; if $R^2$ has the meaning —$COR^3$ M preferably represents halogen, such as, in particular, chlorine or bromine, anhydride and imidazolide; if $R^2$ has the other above mentioned meanings M preferably represents halogen, such as, in particular, chlorine or bromine; alkylsulfonyloxy, such as, in particular, methylsulfonyloxy; and optionally substituted arylsulfonyloxy, such as, in particular, phenylsulfonyloxy, p-chlorophenylsulfonyloxy or tolylsulfonyloxy.

The intermediates of the formulae (Ia), (Ib), (II), (IIa), (IIb), (IIc), (IId), (VII), (VIIa), (VIIb), (VIII), (X), (XI), (XIII), (XIV), (XVI) and (XVII) are new and also subject of the invention. They themselves have insecticidal and acaricidal properties in some cases, for example the compounds of the formula (Ia), (Ib), (XIV) and (XVII).

Process Aα) for the preparation of compounds of the formula (IIa) comprises a process in which compounds of the formula (III) are reacted with compounds of the formula (IV), if appropriate in the presence of a base, if appropriate in the presence of a catalyst and if appropriate in the presence of a diluent, and, if appropriate, the product is subsequently hydrogenated.

Diluents which can be employed are all customary solvents. Substances which can preferably be used are, for example, nitrites, such as acetonitrile and butyronitrile, ethers, such as methyl tert-butyl ether, methyl tert-amyl ether, diisopropyl ether, 1,2-dimethoxyethane, tetrahydrofuran and dioxane.

Bases which can be employed are all customary proton acceptors. Examples which may be mentioned are tertiary amines, such as triethylamine, pyridine, diazabicyclooctane (DABCO), diazabicycloundecane (DBU), as well as alkali metal hydroxides and alkaline earth metal hydroxides. Substances which can preferably be used are alkali metal hydroxides, in particular sodium hydroxide or potassium hydroxide, all of which can also be employed in the form of an aqueous solution.

Phase transfer catalysts may be employed as catalysts. Examples which may be mentioned are quarternary ammonium salts, such as tetraoctylammonium bromide and benzyltriethylammonium chloride.

The reaction temperature can be varied within a substantial range. In general, the process is carried out at temperatures between 20° C. and 100° C., preferably between 25° C. and 70° C.

In general, the reaction is carried out under atmospheric pressure or elevated pressure. In general, the process is carried out under a pressure of between 1 bar and 25 bar, preferably between 1 bar and 6 bar.

The ratio of base to starting substance of the formula (III) can be varied within a substantial range. In principle, catalytic amounts of base suffice, but the base can also be employed in equimolar amounts or in excess. In general, 0.1 to 5 mol, preferably 0.5 to 2 mol, of base are used per mole of compound of the formula (III).

In general, the procedure is followed in which the compound of the formula (III) and the base are introduced into a diluent, the reaction temperature desired is set, and an approximately equimolar amount of the olefin of the formula (IV) is metered in.

If the process is carried out in a sealed vessel or in an autoclave, a certain inherent pressure is established, and this pressure can be elevated by passing in an inert gas such as, for example, nitrogen.

The reaction mixture is worked up in the customary manner, for example by extraction or filtration.

Open-chain compounds of the formula (IV) react with the compounds of the formula (III) by an addition reaction.

Cyclic compounds of the formula (IV) react with the compounds of the formula (III) at the double bond by a substitution reaction. The double bond which then remains can subsequently be hydrogenated, if appropriate, for example using hydrogen (if appropriate under elevated pressure) in the presence of a noble metal catalyst such as, for example, platinum or palladium. The hydrogenation is preferably carried out in a diluent, suitable diluents being all customary solvents such as, for example, (halogeno) hydrocarbons, ethers and alcohols. If Y represents fluorine or chlorine, it is preferred to use aprotic solvents.

Process Aβ) for the preparation of compounds of the formula (IIb) comprises a process in which compounds of the formula (III) are reacted with a difluorohalogenomethane of the formula (V), if appropriate in the presence of a base, if appropriate in the presence of a catalyst and if appropriate in the presence of a diluent.

Diluents which can be employed are all customary solvents. Substances which can preferably be used are, for example, nitrites, such as acetonitrile and butyronitrile, ethers, such as methyl tert-butyl ether, methyl tert-amyl ether, diisopropyl ether, 1,2-dimethoxyethane, tetrahydrofuran and dioxane, or alcohols, such as ethanol, the propanol isomers or the butanol isomers.

Bases which can be employed are all customary proton acceptors. The following can preferably be used: alkali metal hydroxides, such as sodium hydroxide or potassium hydroxide, all of which can also be employed in the form of an aqueous solution.

Phase transfer catalysts may be employed as catalysts. Examples which may be mentioned are quarternary ammonium salts, such as tetraoctylammonium bromide and benzyltriethylammonium chloride, and phosphonium salts, such as tetrabutylphosphonium bromide.

The reaction temperature can be varied within a substantial range. In general, the process is carried out at a temperature between 20° C. and 150° C., preferably between 40° C. and 100° C.

In general, the reaction is carried out under atmospheric pressure or elevated pressure. In general, the process is carried out under a pressure of between 1 bar and 25 bar, preferably between 1 bar and 10 bar.

The ratio of base to starting substance of the formula (III) can be varied within a substantial range. In general, 1 to 10 mol, preferably 1 to 5 mol, of base are employed per mole of compound of the formula (III).

The difluorohalogenomethane of the formula (V) is generally employed in up to 5-fold excess.

Process Aγ) for the preparation of compounds of the formula (IIc) comprises a process in which compounds of the formula (VI) are diazotized and the product is reacted with benzene in the presence of acid and iron powder or in the presence of a base and, if appropriate, in the presence of a diluent.

Suitable diluents are all inert solvents. Alternatively, a larger excess of the reactant benzene, preferably up to 30 mol, particularly preferably up to 5 mol, per mole of the compound of the formula (VI), may be used as the diluent.

If the reaction is carried out in the presence of acid and iron powder, then suitable acids are preferably organic acids such as trichloroacetic acid.

If the reaction is carried out in the presence of a base, suitable bases are, for example, salts of organic acids such as alkali metal acetates, in particular sodium acetate or potassium acetate.

In general, two equivalents of base are employed.

The reaction temperature can be varied within a substantial range. In general, the process is carried out at a temperature between −40° C. and 140° C., preferably between −20° C. and 80° C.

The reaction is generally carried out under atmospheric pressure.

The diazonium salt is generally prepared from the compound of the formula (VI) in the presence of an acid, such as hydrochloric acid or sulfuric acid, in a customary manner by reaction with an alkali metal nitrite, such as sodium nitrite, or an alkyl nitrite, such as pentyl nitrite or methyl nitrite, or by reaction with nitrosyl chloride.

The reaction mixture comprising the product of the formula (IIc) is worked up with the aid of customary methods.

Process Aε) for the preparation of compounds of the formula (IId) comprises a process wherein compounds of the formula (III) are reacted with carbon tetrachloride in the presence of anhydrous hydrofluoric acid, if appropriate in the presence of a diluent.

Suitable diluents are inert organic solvents. An excess of 2 to 3 times the amount of carbon tetrachloride is preferably used as diluent.

The amount of anhydrous hydrofluoric acid can be varied within a substantial range. In general, 2 to 40 mol, preferably 5 to 20 mol, of anhydrous hydrofluoric acid are employed per mole of the compound of the formula (III).

The reaction temperature can be varied within a substantial range. In general, the process is carried out at a temperature between 60° C. and 150° C., preferably between 80° C. and 125° C.

In general, a procedure is followed in which, in an autoclave, the compound of the formula (III) is mixed with carbon tetrachloride and anhydrous hydrofluoric acid, and the mixture is heated to the desired temperature and stirred at the prevailing pressure.

For working-up, the reaction mixture is freed from components of higher volatility, such as hydrofluoric acid, freons and excess carbon tetrachloride, for example by means of distillation.

The residue is taken up in a suitable inert solvent, and the mixture is washed with alkali and purified by distillation.

Process Bα) for the preparation of compounds of the formula (VII) comprises a process in which compounds of the formula (II) are reacted with acetyl chloride in the presence of an acid or Lewis acid and in the presence of a diluent.

Suitable diluents are all customary solvents which are suitable for Friedel-Crafts reactions. Chlorinated hydrocarbons such as, for example, methylene chloride or dichloroethane are preferably used.

Suitable acids or Lewis acids are all those which are suitable for Friedel-Crafts reactions. Aluminum chloride, anhydrous hydrofluoric acid, tetrafluoroboric acid or $BF_3$ etherate are preferably used.

The reaction temperature can be varied within a substantial range. In general, the process is carried out at temperatures between −30° C. and 80° C., preferably between −15° C. and 50° C.

The reaction is generally carried out under atmospheric pressure or under elevated pressure.

Acetyl chloride and the compounds of the formula (II) are generally employed in approximately equimolar amounts.

When the reaction has ended, the product is worked up with the aid of customary methods.

Process Bβ) for the preparation of compounds of the formula (VIIa) comprises a process in which compounds of the formula (IIIa) are reacted with a compound of the formula (IV), if appropriate in the presence of a base, if appropriate in the presence of a catalyst and if appropriate in the presence of a diluent, and, if appropriate, the mixture is subsequently hydrogenated.

As regards base, catalyst, diluent and the other reaction conditions, what has been said in process Aα) applies equally to the present process.

Process Bγ) for the preparation of compounds of the formula (VIIb) comprises a process in which a compound of the formula (IIIa) is reacted with a compound of the formula (V), if appropriate in the presence of a base, if appropriate in the presence of a catalyst and if appropriate in the presence of a diluent.

As regards base, catalyst, diluent and the other reaction conditions, what has been said in process Aβ) applies equally to the present process.

Process Cα) for the preparation of compounds of the formula (VIII) comprises a process in which compounds of the formula (VIII) are chlorinated or brominated, if appropriate in the presence of a diluent.

Suitable diluents are all the solvents which are inert to chlorine and bromine. Examples of diluents which are preferably used are chlorohydrocarbons, such as methylene chloride, chloroform or carbon tetrachloride, or alcohols such as methanol or ethanol.

The reaction temperature can be varied within a substantial range. In general, the process is carried out at a temperature between −30° C. and 50° C., preferably between −10° C. and 25° C.

The reaction is generally carried out under atmospheric pressure.

In general, a procedure is followed in which the compound of the formula (VII) is introduced into a suitable diluent, and an approximately equimolar amount of chlorine or bromine is then metered in at the temperature desired. It is also possible to employ a small excess, or a slightly substoichiometric amount, of halogen.

Process Cβ) for the preparation of compounds of the formula (VIII) comprises a process in which compounds of the formula (II) are reacted with halogenoacetyl chlorides of the formula (IX) in the presence of an acid or Lewis acid and in the presence of a diluent.

Suitable diluents are all customary solvents which are suitable for Friedel-Crafts reactions. Chlorinated hydrocarbons such as, for example, methylene chloride or dichloroethane are preferably used.

Suitable acids or Lewis acids are all those which are suitable for Friedel-Crafts reactions. Aluminum chloride or tetrafluoroboric acid are preferably used.

The temperature can be varied within a substantial range. In general, the process is carried out between −30° C. and 50° C., preferably between −15° C. and 30° C.

The reaction is generally carried out under atmospheric pressure.

In general, the halogenoacetyl chloride of the formula (IX) and the compound of the formula (II) are employed in approximately equimolar amounts.

When the reaction is complete, the product is worked up with the aid of customary methods.

Process D) for the preparation of compounds of the formula (X) comprises a process wherein compounds of the formula (VIII) are reacted with a salt of formic acid, if appropriate in the presence of a catalyst.

Suitable diluents are all customary solvents which are inert under the reaction conditions. The following can preferably be used: hydrocarbons, such as toluene, xylene, mesitylene, cyclohexane, methylcyclohexane, chlorohydrocarbons, such as chlorobenzene, o-dichlorobenzene, carbon tetrachloride, alcohols, such as methanol, ethanol, the propanol isomers, the butanol isomers and the pentanol isomers, ethers, such as diisopropyl ether, tetrahydrofuran, dioxane, nitriles, such as acetonitrile and butyronitrile, amides, such as dimethylformamide, and also strongly polar solvents, such as dimethyl sulfoxide and sulfolane.

If appropriate, the abovementioned diluents can also be used in the form of a mix- ture with water, if appropriate in the presence of a phase transfer catalyst, e.g. quaternary ammonium salts, such as tetraoctylammonium bromide or benzyltriethylammonium chloride.

Salts of formic acid which can preferably be used are sodium formate and potassium formate.

The reaction temperature can be varied within a substantial range. In general, the process is carried out at temperatures between 50° C. and 200° C., preferably between 80° C. and 160° C.

In general, a procedure is followed in which the compound of the formula (VIII) is heated with 1 to 20 mol, preferably 1 to 5 mol, of formate in a diluent, then, if appropriate, water is added, and the phases are separated and the diluent is distilled off.

Process E for the preparation of compounds of the formula (XI) comprises a process wherein compounds of the formula (X) are reacted with the compound of the formula (XII), if appropriate in the presence of a diluent.

Suitable diluents are all customary solvents. Examples of diluents which are preferably used are alcohols, such as methanol, ethanol, the propanol, butanol and pentanol isomers, or ethers, such as diisopropyl ether, tetrahydrofuran or dioxane, all of which can, if appropriate, be employed in the form of a mixture with water.

O-methylhydroxylamine, of the formula (XII), can be employed in the form of the free base or else as the salt of an acid. In the latter case, the process is carried out in the presence of a base, preferably sodium acetate. The compound of the formula (XII) is generally employed in equimolar amounts.

The reaction temperature can be varied within a substantial range. In general, the process is carried out at temperatures between −20° C. and 100° C., preferably between 0° C. and 60° C.

The reaction is generally carried out under atmospheric pressure.

Working-up is carried out in the customary manner, for example by filtration or extraction.

Process F) for the preparation of compounds of the formula (XIII) comprises a process wherein the compound of the formula (XI) is reacted with a reducing agent in the presence of an acid and, if appropriate, in the presence of a diluent.

Suitable diluents are all solvents which are inert to the reactants. Diluents which are preferably used are ethers such as, for example, diisopropyl ether, methyl tertbutyl ether, tetrahydrofuran, 1,2-dimethoxyethane and dioxane.

The preferred reducing agent is sodium boranate used in an equimolar amount or in excess.

The preferred acid is trifluoroacetic acid used in an equimolar amount or in excess.

The reaction temperature can be varied within a substantial range. In general, the beginning of the reaction is carried out at temperatures between 0° C. and 50° C., and the temperature is raised during the course of the reaction, if appropriate to up to 120° C.

The reaction is generally carried out under atmospheric pressure.

Working-up is carried out with the aid of customary methods.

The reaction product of the formula (XIII) is preferably isolated in the form of salts, for example the hydrochlorides.

Process Gα) comprises a process in which the compound of the formula (XIII) is reacted with 2-A, 6-B- benzoyl chloride, if appropriate in the presence of a base and if appropriate in the presence of a diluent.

Diluents which can be employed are all solvents which are inert to these compounds. The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, in addition carboxylates, such as ethyl acetate, and also strongly polar solvents, such as dimethyl sulfoxide and sulfolane. The reaction can also be carried out in the presence of water if the acid halide is sufficiently stable to hydrolysis.

Suitable bases in the reaction are all customary acid acceptors. The following can preferably be used: tertiary amines, such as triethylamine, pyridine, diazabicyclooctane (DABCO), diazabicycloundecene (DBU), diazabicyclononene (DBN), Hünig base and N,N-dimethyl-aniline, furthermore alkaline earth metal oxides, such as magnesium oxide and calcium oxide, moreover alkali metal carbonates and alkaline earth metal carbonates, such as sodium carbonate, potassium carbonate and calcium carbonate, and alkali metal hydroxides or alkaline earth metal hydroxides, such as sodium hydroxide or potassium hydroxide.

The reaction temperatures can vary within a substantial range. In general, the reaction is carried out at temperatures between −20° C. and +100° C., preferably between 0° C. and 30° C.

The reaction is generally carried out under atmospheric pressure.

When carrying out the process, the starting substances of the formula (XIII) and 2,6-difluorobenzoyl chloride are generally employed in approximately equivalent amounts. However, it is also possible to employ the carboxylic acid halide in a larger excess (up to 5 mol). Working-up is carried out by customary methods.

Process Gβ) for the preparation of the compound of the formula (XIV) comprises a process wherein (Step 1) the compound of the formula (II) is first reacted with a compound of the formula (XV) in the presence of an acidic catalyst and if appropriate in the presence of a diluent and then (Step 2) the resulting compound of the formula (XVI) is reacted with a reducing agent in the presence of a diluent.

Suitable diluents for the first step are all solvents which are inert to the reactants.

The following are preferably used: hydrocarbons such as toluene, xylene, tetralin, halogenohydrocarbons such as methylene chloride, chloroform, chlorobenzene, o-dichlorobenzene, ethers such as diisopropyl ether, methyl tert-butyl ether, tetrahydrofuran, dioxane, dimethoxyethane, ketones such as acetone or methyl ethyl ketone, alcohols such as methanol, ethanol and propanol, amides such as dimethylformamide, and sulfoxides such as dimethyl sulfoxide.

Acidic catalysts which are suitable are, in principle, all inorganic or organic acids or Lewis acids. Examples of acids which are preferably used are sulfuric acid, methanesulfonic acid, benzenesulfonic acid, aluminum chloride, titanium tetrachloride, phosphorus oxychloride, boron trifluoride etherate. If appropriate, an excess of acid can also act as diluent.

The reaction temperature can be varied within a substantial range. In general, the process is carried out at temperatures between −20° C. and 150° C., preferably between 0° C. and 50° C.

The reaction is generally carried out under atmospheric pressure.

The compound of the formula (II) and the compound of the formula (XV) are generally employed in equimolar amounts, but it is also possible to use an excess of one or the other compound.

Suitable diluents in the second step are, in particular, alcohols and ethers. Examples which may be mentioned are methanol, ethanol, the propanol, butanol and pentanol isomers, furthermore diethyl ether, diisopropyl ether, methyl tert-butyl ether, tetrahydrofuran, dioxane and dimethoxyethane.

The preferred reducing agent used is sodium borohydride in an amount of 1 to 5 mol per mole of the compound of the formula (XVI).

If the compound of the formula (XVI) is in the form of an acid ($R^6$=H), this acid must be converted into an alkyl ester before the reaction with sodium borohydride is carried out.

The reaction temperature can be varied within a substantial range. In general, the process is carried out at temperatures between 20° C. and 150° C., preferably between 50° C. and 100° C.

The reaction is generally carried out under atmospheric pressure.

The product is worked up with the aid of customary methods.

Process Hα) for the preparation of compounds of the formula (XVII) comprises a process wherein compounds of the formula (XIV) are reacted with a chlorinating agent, if appropriate in the presence of a diluent.

Suitable diluents are all inert organic solvents. Diluents which are preferably used are hydrocarbons such as toluene, xylene, hexane, cyclohexane, halogenohydrocarbons such as chlorobenzene, chloroform, methylene chloride and ethers such as diethyl ether, diisopropyl ether, dimethoxyethane, tetrahydrofuran and dioxane.

Suitable chlorinating agents are all reactants which can conventionally be used for this purpose. Examples which may be mentioned are thionyl chloride, phosgene and phosphorus oxychloride, all of which are generally employed in at least equimolar amounts.

The reaction temperature can be varied within a substantial range. In general, the process is carried out at temperatures between 0° C. and 120° C., preferably between 20° C. and 100° C.

If appropriate, the reaction is carried out in the presence of a base, in particular a tertiary amine such as, for example, triethylamine or pyridine.

Process Hβ for the preparation of compounds of the formula (XVII) comprises a process wherein compounds of the formula (II) or (IIe) are reacted with compounds of the formula (XVIII) in the presence of an acidic catalyst and if appropriate in the presence of a diluent.

Suitable diluents are all solvents which are inert to the reactants.

The following are preferably used: hydrocarbons such as toluene, xylene, tetralin, halogenohydrocarbons such as methylene chloride, chloroform, chlorobenzene, o-dichlorobenzene, ethers such as diisopropyl ether, methyl tert-butyl ether, tetrahydrofuran, dioxane, dimethoxyethane, ketones such as acetone or methyl ethyl ketone, alcohols such as methanol, ethanol, propanol, amides such as dimethylforma mide, and sulfoxides such as dimethyl sulfoxide.

Suitable acidic catalysts are, in principle, all inorganic or organic acids or Lewis acids. Examples of acids which are preferably used are sulfuric acid, methanesulfonic acid, benzenesulfonic acid, anhydrous hydrofluoric acid, aluminum chloride, titanium tetrachloride, phosphorus oxychloride or boron trifluoride etherate. If appropriate, an excess of acid can also act as diluent.

The reaction temperature can be varied within a substantial range. In general, the process is carried out at temperatures between −20° C. and 150° C., preferably between 0° C. and 80° C.

The reaction is generally carried out under atmospheric pressure or under elevated pressure.

In general, the compounds of the formulae (II) or (IIe) and the compound of the formula (XVIII) are employed in equimolar amounts; however, it is also possible to use an excess of one or the other compound.

Process I) for the preparation of the compounds of the formula (I) comprises a process wherein the compounds of the formula (XVII) are cyclized in the presence of a base, if appropriate in the presence of a catalyst and if appropriate in the presence of a diluent.

Suitable diluents are all inert organic solvents. If appropriate, they may be used in the form of a mixture with water. The following are preferably used: hydrocarbons such as toluene, xylene, tetralin, hexane, cyclohexane, halogenohydrocarbons such as methylene chloride, chloroform, chlorobenzene, o-dichlorobenzene, alcohols such as methanol, ethanol, glycol, the propanol, butanol and pentanol isomers, ethers such as diethyl ether, diisopropyl ether, dimethoxyethane, tetrahydrofuran, dioxane, nitriles such as acetonitrile or butyronitrile, amides such as dimethylformamide, sulfoxides such as dimethyl sulfoxide, and furthermore sulfolane. Alcohols are particularly preferably used.

Suitable bases are all customary acid acceptors.

The following can preferably be used: tertiary amines such as triethylamine, pyridine, DABCO, DBU, DBN, N,N-dimethylaniline, furthermore alkaline earth metal oxides such as magnesium oxide and calcium oxide, in addition alkali metal carbonates and alkaline earth metal carbonates such as sodium carbonate, potassium carbonate and calcium carbonate, alkali metal hydroxides such as sodium hydroxide and potassium hydroxide, furthermore alcoholates such as sodium ethanolate or potassium tert-butylate.

If appropriate, the process is carried out in the presence of a phase transfer catalyst. Examples of suitable phase transfer catalysts are ammonium compounds such as tetraoctylammonium bromide or benzyltriethylammonium chloride.

The reaction temperature can be varied within a substantial range. In general, the process is carried out at temperatures between −10° C. and 150° C., preferably between 0° C. and 100° C.

The reaction is generally carried out under atmospheric pressure.

In general, an equimolar amount of base is employed. However, it is also possible to use an excess of base.

Working-up is carried out in the customary manner.

Process J) for the preparation of compounds of the formula (Ib) is characterized in that the compounds of the formula (Ia) are hydrolyzed.

Process J) is preferably carried out in the presence of a diluent. Preferred diluents which are used are water/alcohol mixtures, such as, for example, water/methanol, water/ethanol or water/propanol, or water/amide mixtures such as, for example, water/dimethylformamide (DMF) or water/dimethylacetamide.

Process J) is carried out in the presence of a base. Suitable bases are inorganic and organic bases, in particular alkali metal hydroxides, such as sodium hydroxide or potassium hydroxide, or ammonia.

The reaction temperature can be varied within a substantial range. In general, the process is carried out at temperatures between −10° C. and 60° C., preferably between 0° C. and 40° C. The reaction is generally carried out under atmospheric pressure.

Process Kα) is characterized in that a compound of the formula (Ib) is reacted with a compound of the formula (XIX), if appropriate in the presence of a diluent and if appropriate in the presence of a base.

Diluents which can be employed are all solvents which are inert to these compounds. The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, furthermore ketones, such as acetone and methyl isopropyl ketone, in addition ethers, such as diethyl ether, tetrahydrofuran and dioxane, moreover carboxylic esters, such as ethyl acetate, and also strongly polar solvents, such as dimethyl sulfoxide and sulfolane. If the acid halide is sufficiently stable to hydrolysis, the reaction can also be carried out in the presence of water.

Suitable acid-binding agents for the reaction are all customary acid acceptors. The following can preferably be used: tertiary amines, such as triethylamine, pyridine, diazabicyclooctane (DABCO), diazabicycloundecene (DBU), diazabicyclononene (DBN), Hünig base and N,N-dimethyianiline, furthermore alkaline earth metal oxides, such as magnesium oxide and calcium oxide, in addition alkali metal carbonates and alkaline earth metal carbonates, such as sodium carbonate, potassium carbonate and calcium carbonate, and alkali metal hydroxides or alkaline earth metal hydroxides, such as sodium hydroxide or potassium hydroxide.

The reaction temperatures can be varied within a substantial range. In general, the process is carried out at temperatures between −20° C. and +100° C., preferably between 0° C. and 30° C.

The reaction is generally carried out under atmospheric pressure.

When carrying out the process, the starting substances of the formulae (Ib) and (XIX) are generally used in approximately equivalent amounts. However, it is also possible to employ the compound of the formula (XIX) in a larger excess (up to 5 mol). Working-up is carried out by customary methods.

Process Kβ) is characterized in that a compound of the formula (Ib) is reacted with a compound of the formula (IV), if appropriate in the presence of a base, if appropriate in the presence of a catalyst and if appropriate in the presence of a diluent, and, if appropriate, the product is subsequently hydrogenated.

What has been said above for process Aα) with regard to diluent, base, catalyst, temperature, pressure, ratio of base to starting substance of the formula (Ib), carrying out the process and working-up the product applies analogously.

Process Kγ) is characterized in that a compound of the formula (Ib) is reacted with a difluorohalogenomethane of the formula (V), if appropriate in the presence of a base, if appropriate in the presence of a catalyst and if appropriate in the presence of a diluent.

What has been said above for process Aβ) with regard to diluent, base, catalyst, temperature, pressure and ratio by weight of the substances involved applies analogously.

Process Kδ) is characterized in that a compound of the formula (Ib) is reacted with carbon tetrachloride in the presence of hydrofluoric acid, if appropriate in the presence of a diluent.

What has been said above for process Aδ) with regard to diluent, amount of hydrofluoric acid, temperature, carrying out the process and working up the product applies analogously.

Process Kε) is characterized in that a compound of the formula (Ib) is reacted with a compound of the formula (XX), if appropriate in the presence of a diluent and if appropriate in the presence of a base.

Diluents which are suitable are all customary solvents. The following can preferably be used: optionally halogenated, aromatic or aliphatic hydrocarbons, ketones, nitrites and amides. Examples which may be mentioned are toluene, acetone, acetonitrile, dimethylformamide and dimethylacetamide.

Bases which are suitable are all customary inorganic and organic bases. Examples which may be mentioned are tertiary amines such as triethylamine, DBN, DBU, DABCO, alkali metal hydroxides and alkaline earth metal hydroxides such as, for example, sodium hydroxide, potassium hydroxide and calcium hydroxide, and also alkali metal carbonates and alkaline earth metal carbonates such as, for example, sodium carbonate or potassium carbonate.

The reaction temperature can be varied within a substantial range. In general, the process is carried out at temperatures between −20° C. and 100° C., preferably between 0° C. and 60° C.

The reaction is generally carried out under atmospheric pressure.

In general, the compounds of the formula (Ib) and the compounds of the formula (XX) are employed in approximately equimolar amounts. However, it is also possible to use an excess of the compounds of the formula (XX).

The active compounds are suitable for combating animal pests, preferably arthropods and nematodes, in particular insects and arachnids, encountered in agriculture, in forestry, in the protection of stored products and of materials, in veterinary medicine and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera spec.*

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis, Schistocerca gregaria* and Supella spp.

From the order of the Dermaptera, for example, *Forficula auricularia.*

From the order of the Isoptera, for example, Reticulitermes spp.

From the order of the Anoplura, for example, *Phylloxera vastatrix,* Pemphigus spp., Phthirus spp., Pediculus spp., Haematopinus spp., Linognathus spp. and Solenopotes spp.

From the order of the Mallophaga, for example, Trichodectes spp. and Damalinea spp., Trimenopon spp., Monopon spp., Trinoton spp., Bovicola spp., Werneckiella spp., Lepikentron spp. and Felicola spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus,* Triatoma spp. and Panstrongylus spp.

From the order of the Homoptera, for example, *Aleurodes brassicae, Bemisia tabaci, Trialeurodes vaporariorum,*

Aphis gossypii, Brevicoryne brassicae, Cryptomyzus ribis, Aphis fabae, Doralis pomi, Eriosoma lanigerum, Hyalopterus arundinis, Macrosiphum avenae, Myzus spp., Phorodon humuli, Rhopalosiphum padi, Empoasca spp., Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus spp. and Psylla spp.

From the order of the Lepidoptera, for example, Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Agrotis spp., Euxoa spp., Feltia spp., Earias insulana, Heliothis spp., Spodoptera exigua, Mamestra brassicae, Panolis flammea, Prodenia litura, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima and Tortrix viridana.

From the order of the Coleoptera, for example, Anobium punctatum, Rhizopertha dominica, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solsti tialis and Costelytra zealandica.

From the order of the Hymenoptera, for example, Diprion spp., Hoplocampa spp., Lasius spp., Monomorium pharaonis and Vespa spp.

From the order of the Diptera, for example, Aedes spp., Anopheles spp., Culex spp., Drosophila melanogaster, Musca spp., Fannia spp., Calliphora spp., Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae, Tipula paludosa, Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Hydrotaea spp., Stomoxys spp., Haematobia spp., Morellia spp., Fannia spp., Glossina spp., Calliphora spp., Wohlfahrtia spp., Sarcophaga spp., Oestrus spp., Hypoderma spp., Gasterophilus spp., Hippobosca spp., Lipoptena spp., Melophagus spp. and Muscina spp.

From the order of the Siphonapterida, for example, Xenopsylla spp., Ceratophyllus spp., Pulex spp. and Ctenocephalides spp.

From the order of the Arachnida, for example, Scorpio maurus and Latrodectus mactans.

From the order of the Acarina, for example, Myocoptes spp., Otodectes spp., Acarus siro, Argas spp., Ornithodoros spp., Omithonyssus spp., Dermanyssus spp., Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychus spp., Dermacentor spp., Haemaphysalis spp., Raillietia spp., Pneumonyssus spp., Sternostorma spp. and Varroa spp.

From the order of the Actinedida (Prostigmata) and Acaridida (Astigmata), for example, Acarapis spp., Cheyletiella spp., Ornithocheyletia spp., Myobia spp., Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Otodectes spp., Sarcoptes spp., Notoedres spp., Knemidocoptes spp., Cytodites spp. and Laminosioptes spp.

The active compounds according to the invention are distinguished by a powerful insecticidal and acaricidal activity.

They can be particularly successfully to combat insects which are harmful to plants, such as, for example, against the larvae of the mustard beetle (Phaedon cochleariae) or against the larvae of the green rice leafhopper (Nephotettix cincticeps) or against the larvae of the cabbage moth (Plutella maculipennis).

The active compounds can be converted to the customary formulations, such as solutions, emulsions, wettable powders, suspensions, powders, dusts, pastes, soluble powders, granules, suspoemulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates as well as albumen hydrolysis products, as dispersing agents there are suitable: for example lignin-sulfite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compound according to the invention can be present in its commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphates, carbamates, carboxylates, chlorinated hydrocarbons, phenylureas and substances Examples of particularly favorable mixture components are the following cornpounds:

Fungicides 2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)-benzamide; (E)-2-methoxyimino-N-methyl-2-(2 phenoxyphenyl)-acetamide; 8-hydroxyquinoline sulfate; methyl (E)-2-{2-[6-(2-cya nophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulfide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluorornide, fluquinconazole, flusilazole, flusulfamide, flutolanil, flutriafol, folpet, fosetylaluninum, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulfate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, phthalide, pimaricin, piperalin, polycarbamate, polyoxin, probenazole, prochloraz, procymidone, propamocarb, propiconazole, propineb, pyrazophos, pyrifenox, pyrimethanil, pyroquilon, quintozene (PCNB), sulfur and sulfur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram Bactericides bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulfate and other copper preparations.

Insecticides/Acaricides/Nematicides abamectin, AC 303 630, acephate, acrinathrin, alanycarb, aldicarb, alphamethrin, amitraz, avermectin, AZ 60541, azadirachtin, azinphos A, azinphos M, azocyclotin, Bacillus thuringiensis, bendiocarb, benfuracarb, bensultap, betacyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton M, demeton S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenpbos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lambda-cyhalothrin, lufenuron, malathion, mecarbam, mevinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram omethoate, oxamyl, oxydemethon M, oxydeprofos, parathion A, parathion M, permethrin, phenthoate, phorate, phosalone, phosmet, phosphaindon, phoxim, pirimicarb, pirimiphos M, pirimiphos A, profenofos, promecarb, propaphos, propoxur, prothiofos, prothoate, pymetrozin, pyraclophos, pyridaphenthion, pyresmethrin, pyrethrum, pyridaben, pyrimidifen, pyriproxifen, quinalphos,

RH 5992, salithion, sebufos, silafluofen, sulfotep, suiprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacrb, vamidothion, XMC, xylylcarb, YI 5301/5302, zetamethrin.

Herbicides for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxyphenoxy-alkanoic esters such as, for example, diclofopmethyl, fenoxaprop-ethyl, fluazifop-butyl, haloxyfopmethyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such 1 as, for example, bromoxynil, dichlobenil and ioxynil; oxyacetamides such as, for example, mefenacet; sulfonylureas such as, for example, amidosulfuron, bensulfuron-methyl, chlorimuronethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryn, terbutryn and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulfosate and tridiphane.

The active compound according to the invention can furthermore be present in its commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

The active compounds according to the invention not only act against plant pests, hygiene pests and stored-product pests, but also, in the veterinary medicine sector, against animal parasites (ectoparasites) such as scaly ticks, Argasidae, scab mites, Trombidae, flies (stinging and sucking), parasitic fly larvae, lice, hair lice, bird lice and fleas. For example, they show an outstanding activity against ticks such as, for example, *Boophilus microplus*.

The active compounds of the formula (I) according to the invention are also suitable for combating arthropods which attack agricultural livestock such as, for example, cattle, sheep, goats, horses, pigs, donkeys, camels, buffalo, rabbits, chikkens, turkeys, ducks, geese, honey bees, other domestic animals such as, for example, dogs, cats, cage birds, aquarium fish, and so-called experimental animals such as, for example, hamsters, guinea pigs, rats and mice. By combating these arthropods, it is intended to reduce deaths and decreasing performance (in meat, milk, wool, hides, eggs, honey and the like), so that more economical and simpler animal keeping is possible by using the active compounds according to the invention.

In the veterinary sector, the active compounds according to the invention are applied in a known manner by means of enteral administration in the form of, for example, tablets, capsules, drinks, drenches, granules, pastes, boli, the feed-through method, suppositories, by parenteral administration, such as, for example, by means of an injection (intramuscular, subcutaneous, intravenous, intraperitoneal and the like), implants, by means of nasal application, by means of dermal application in the form of, for example, immersing or dipping, spraying, pouring-on and spotting-on, washing, dusting, and with the aid of shaped articles which comprise active compound, such as collars, ear tags, tail marks, limb bands, halters, marking devices and the like.

When used for cattle, poultry, domestic animals and the like, the active compounds of the formula (I) can be applied in the form of formulations (for example powders, emulsions, flowables) which comprise 1 to 80% by weight of active compounds, either directly or after diluting them 100 to 10,000-fold, or they can be used in the form of a chemical bath.

The preparation and use of the active compounds according to the invention can be seen from the examples which follow.

PREPARATION EXAMPLES

Example (I-1)

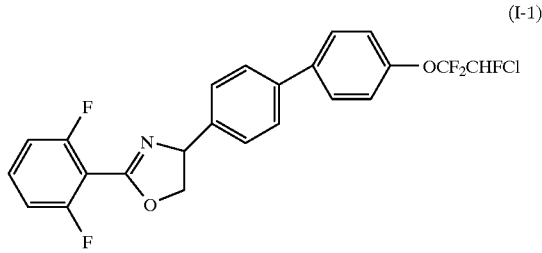

(I-1)

6.1 g (0.012 mol) of the compound of Example (XVII-1) are suspended in 50 ml of dry methanol. 6.4 g (0.048 mol) of 30% strength sodium hydroxide solution are added dropwise without cooling, during which process the temperature rises to 27° C. The mixture is heated at the boil for approximately 20 minutes and then cooled. The mixture is filtered, and the filtrate is washed with water and dried.

Yield: 4.8 g of white crystals (84% of theory)

M.p.: 101–103° C.

Example (I-2)

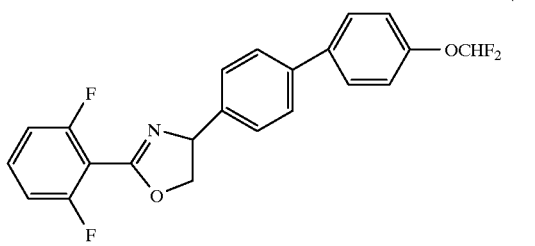

(I-2)

17.6 g (0.042 mol) of 2,6-difluoro-N-[2-hydroxyethyl-1-phenyl-4-(4'-difluoromethoxyphenyl)]-benzamide of Example (XIV-1) are suspended in 150 ml of toluene, 20 g (0.168 mol) of thionyl chloride are added dropwise, and the mixture is heated to 70° C. The mixture is held at this temperature for 1.5 hours and then allowed to cool, and the toluene is distilled off in vacuum. The residue is dissolved in 150 ml of methanol. 22.4 g (0.168 mol) of 30% strength sodium hydroxide solution are then added, and the mixture is heated for 20 minutes at 70° C. After cooling, the mixture is concentrated, the product is taken up in methylene chloride, and the mixture is washed three times with water. Drying and concentrating give 14.9 g of yellow crystals which are purified over silica gel (petroleum ether/ethyl acetate 1:1). 13.0 g of white crystals of m.p. 112° C. are obtained.

Yield: 82% of theory.

The following compounds of the formula (I)

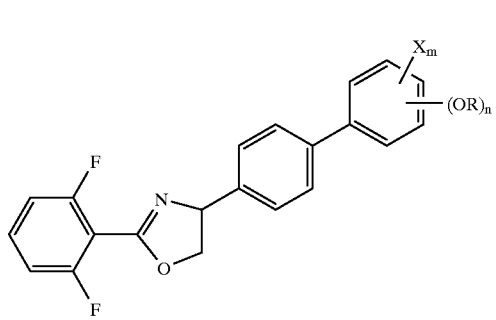

(I)

are obtained analogously to Example I-1 or I-2 and in accordance with the general preparation instructions.

TABLE 1A

| | (n = 1, m = 0) | | |
|---|---|---|---|
| Ex. No. | OR | M.p. [° C.] | Yield (% of theory) |
| I-3 | 4-OCF$_2$CF$_2$H | 106 | 87 |
| I-4 | 4-OCF$_2$CHFCF$_3$ | 86–90 | 64 |
| I-5 | 4-OCF$_2$Cl | 115 | 90 |

TABLE 1A-continued

| | (n = 1, m = 0) | | |
|---|---|---|---|
| Ex. No. | OR | M.p. [° C.] | Yield (% of theory) |
| I-6 | 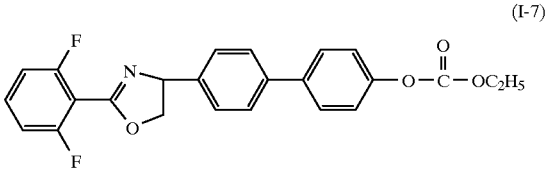 | | |

Example (I-7)

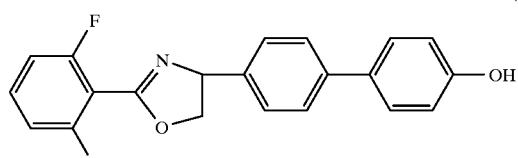

(I-7)

4 ml (0.045 mol) of 50% strength sodium hydroxide solution are added dropwise at 5° C. to 19.8 g (0.043 mol) of the compound of Example (XVII-3) in 120 ml of dimethylformamide. After 2 hours at room temperature, the batch is stirred into 500 ml of ice-water and the crystals which have precipitated are filtered off with suction.

Yield: 15.1 g (83% of theory), m.p.: 98 to 100° C.

Example (I-8)

(I-8)

10.9 g (0.026 mol) of the compound of Example (I-7) are suspended in 50 ml of methanol, and 35.4 ml (0.52 mol) of 25% strength aqueous ammonia solution are then added dropwise at room temperature. After 28 hours at room temperature, the precipitate is filtered off with suction and washed with a little methanol. Yield 7.6 g (97.4% of theory), m.p. 180 to 182° C.

Example (I-9)

One-pot reaction in DMF

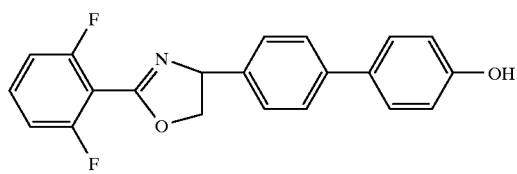
(I-9)

9.6 g of the compound of Example (XVII-3) in DMF are treated with sodium hydroxide solution as described in Example (I-7), and the mixture is then neutralized at 5° C. using dilute hydrochloric acid. After the corresponding amount of ammonia solution (cf. Example I-8) has been added, the mixture is stirred for 15 hours, introduced into ice-water and filtered off with suction. Yield 7 g (94.5% of theory).

Example (I-10)

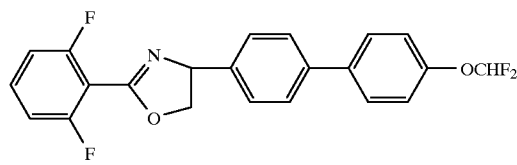
(I-10)

Difluorochloromethane is passed for 3 hours at 40 to 50° C. into a solution of 1.2 g (3.4 mmol) of the compound of Example (I-8) and 2.7 g (50 mmol) KOH in 20 ml of isopropanol. After the mixture has cooled, it is poured into 100 ml of ice-water and extracted twice using in each case 50 ml of methylene chloride, the extract is dried, the solvent is distilled off. After chromatography on silica gel using petroleum ether/ethyl acetate 1/1 as the eluent, 0.8 g (50% of theory) of colorless crystals of m.p. 112° C. is obtained.

Example (I-11)

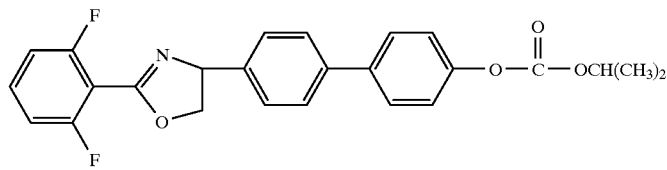
(I-11)

1.4 ml (0.01 mol) of triethylamine is added to 3.5 g (0.01 mol) of the compound of Example (I-8), suspended in 20 ml of ethyl acetate, and 1.2 g (0.01 mol) of isopropyl chloroformate is then added dropwise in the course of 15 minutes, during which process the temperature of the reaction mixture climbs to 30° C. The mixture is stirred for 18 hours at room temperature and washed with 20 ml of water, the organic phase is dried, and, after concentration, the organic phase is chromatographed on silica gel using methylene chloride as the eluent. Yield 2.1 g (48% of theory) m.p. 104° C.

The following compounds of the formula (I)

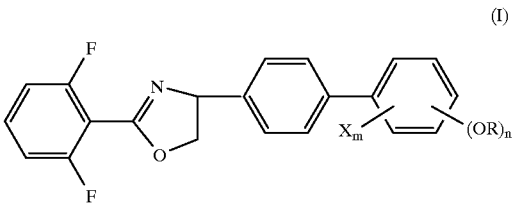
(I)

are obtained analogously or following the general information on preparation:

TABLE 1B (m = 0, n = 1)

| Ex. No. | OR | M.p. [° C.] |
|---|---|---|
| I-12 | 4-OC—C(CH₃)₃ (C=O) | 118–20 |
| I-13 | 4-OC—CH₃ (C=O) | 140–44 |
| I-14* | 4-O-nC₄H₉ | 102 |
| I-15 | 4-O—CH₂—C≡CH | 128–30 |
| I-16* | 4-OCH₃ | 124 |
| I-17 | 4-OCH₂—CH=CH—CH₂C(CH₃)₂—CH₂—C(CH₃)₃ | oil |
| I-18 | 4-OCH₂CH=CH—CH₃ | 126–128 |
| I-19 | 4-O—CH₂—(2,2-dichlorocyclopropyl) | 110–112 |
| I-20 | 4-O—CH₂—cyclohexyl | 129–130 |
| I-21 | 4-O—CH₂—phenyl | 143–145 |
| I-22 | 4-O—CH₂—(4-chlorophenyl) | 195–197 |

| | | Fp. [° C.] |
|---|---|---|
| I-23 | 4-O—(CH₂)₂—phenyl | 78–80 |
| I-24 | 4-O—CH₂—(2,2-dichloro-1-methylcyclopropyl) | log P: 5,23 |
| I-25 | 4-O—CH₂—cyclopropyl | 142 |
| I-26 | 4-O—(CH₂)₃—phenyl | 140–142 |
| I-27 | 4-O—CH₂—(4-tert-butylphenyl) | 138–140 |
| I-28 | 4-O—(CH₂)₃—C≡CH | 105–108 |
| I-29* | 4-O-nC₃H₇ | 138–140 |
| I-30* | 4-O—CH(CH₃)CH₂CH₃ | 50 |
| I-31 | 4-O—CH₂—CH=CH₂ | 130 |

TABLE 1B-continued
(m = 0, n = 1)
| Ex. No. | OR | m.p. [° C.] |
|---|---|---|
| I-32* | 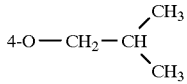 4-O—CH₂—CH(CH₃)CH₃ | 115 |
| I-33* | 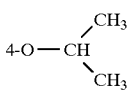 4-O—CH(CH₃)CH₃ | 123 |
| I-34 | 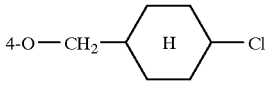 4-O—CH₂—(cyclohexyl)—Cl | 100–110 |
| I-35 | 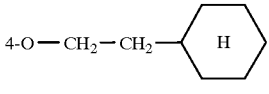 4-O—CH₂—CH₂—(cyclohexyl) | 68 |
| I-36 | 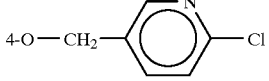 4-O—CH₂—(2-chloropyridyl) | 140–45 |
*Examples for the use of the compound of Example I-8.
Example I-37
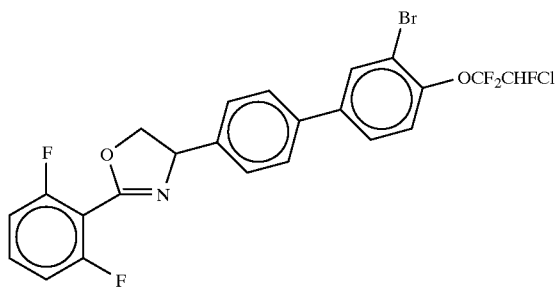
$n_D^{20} = 1.585$
Example I-38
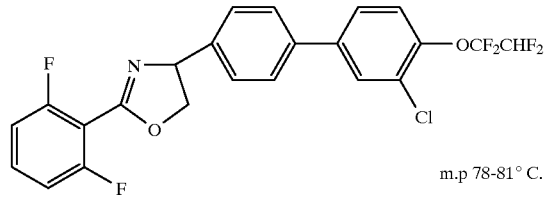
m.p 78-81° C.
TABLE 1B
| Ex. No. | OR | m.p. [° C.] |
|---|---|---|
| I-39 | 4-OCH₂—C(CH₃)=CH₂ | 135–138 |
TABLE 1B-continued
| Ex. No. | OR | m.p. [° C.] |
|---|---|---|
| I-40 | 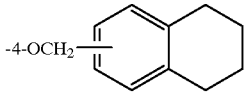 -4-OCH₂—(tetrahydronaphthyl) mixture of isomers | 90–95 |
| I-41 |  -4-OCH₂—(naphthyl) | 152–154 |

TABLE 1B-continued

| Ex. No. | OR | m.p. [° C.] |
|---|---|---|
| I-42 | 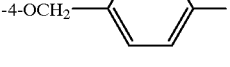 | 138–140 |
| I-43 | 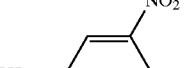 | 132–134 |
| I-44 | 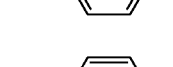 | 126–130 |
| I-45 | 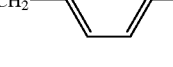 | 130–132 |
| I-46 | 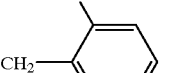 | 92–95 |
| I-47 | 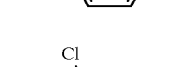 | 180–190 |
| I-48 | 4-O—CO—NH—C(CH$_3$)$_3$ | 120–125 |
| I-49 | 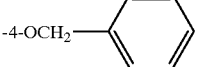 | 168–171 |
| I-50 | 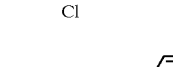 | 118–120 |
| I-51 |  | 178–180 |

Example I-52

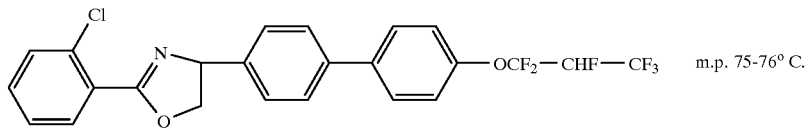 m.p. 75-76° C.

Preparation of starting compounds

Example (IIa-1)

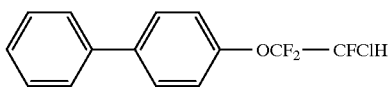 (IIa-1)

250 g of 4-hydroxybiphenyl in 1000 ml of acetone and 50 g of pulverulent sodium hydroxide are introduced into a stirring apparatus equipped at the bottom of the reaction vessel with a gas inlet tube, and the reaction mixture is heated to the boil. Trifluorochloroethylene is subsequently passed in until the mixture is saturated. After the mixture has cooled to room temperature, 2000 ml of water are metered in, and the organic phase which is separating off is removed. After drying, the product is distilled; boiling range: 170–174° C./20 mbar. Yield: 295 g.

Example (IIa-2)

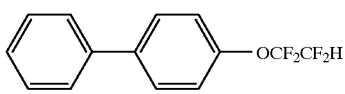 (IIa-2)

250 g of 4-hydroxy-biphenyl, 1000 ml of N-methylpyrrolidone and 50 g of pulverulent sodium hydroxide are introduced into a stirring apparatus equipped with a gas inlet tube, and the mixture is heated to 130° C. Tetrafluoroethylene is then passed in until no more tetrafluoroethylene is taken up. After the batch has cooled to room temperature, it is stirred into 3000 ml of water, and the solid is filtered off with suction, washed with water and dried in vacuo.

391 g of 4-tetrafluoroethoxy-biphenyl=98% of theory are obtained; melting point 65° C.

Example (IIa-3)

Analogously, 250 g of 4-hydroxybiphenyl are reacted with hexafluoropropene to give 4-hexafluoropropoxy-biphenyl.

Yield: 180 g; boiling point: 96–98° C./0.3 mbar, melting point: 60° C.

Example (IIb-1)

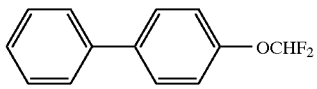 (IIb-1)

51.1 g (0.3 mol) of 4-hydroxybiphenyl are dissolved in 250 ml of dioxane, and 38.3 ml of 45% strength sodium hydroxide solution are added. The mixture is heated to 60° C., and 100 g (1.15 mol) of difluorochloromethane are then passed in at this temperature. After cooling, 75 ml of water are added, the insoluble precipitate is filtered off with suction, and the aqueous phase is extracted three times using tert-butyl methyl ether. The combined organic phases are dried and concentrated. This gives 55.9 g of crude product which still contains 20.9% of starting phenol, which is removed using sodium hydroxide solution.

Yield: 40 g (60% of theory)

M.p.: 35° C.

Example (IIe-1)

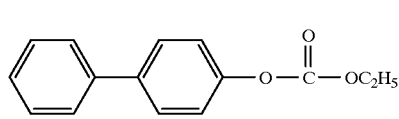

22 g (0.2 mol) of ethyl chloroformate are added dropwise at 10° C. in the course of 15 minutes to 34 g (0.2 mol) of 4-hydroxybiphenyl and 28 ml of triethylamine in 200 ml of ethyl acetate. Stirring is continued for 30 minutes at room temperature, the precipitate is filtered off with suction, and the liquid phase is washed using 200 ml of water, dried and concentrated in vacuo. The residue is taken up in 50 ml of diisopropyl ether and the crystals are filtered off with suction. Yield 47.5 g (98.5% of theory), m.p. 70° C.

Example (Ic-1)

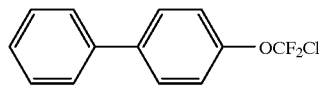

800 ml of benzene, 40 g of Fe powder and 350 g of 4-difluoromethoxyaniline are introduced into the reaction vessel, and a solution of 1000 g of trichloroacetic acid in 1600 ml of benzene is added dropwise at 30–38° C. in the course of 5 hours. At the same time, 210 g of sodium nitrite are added in portions (12 g every 15 minutes). The reaction is slightly exothermic, and gas is evolved during the addition. At the end of the addition, stirring is continued for approximately 20 hours at room temperature. The mixture is subsequently heated up to reflux temperature (75–76° C.) in accordance with the evolution of gas, and stirring is continued until the evolution of gas has ended (approximately 4 hours). The batch is cooled, 2.4 liters of 5% strength hydrochloric acid are added, and benzene is first distilled off until the internal temperature has reached 100° C. This is followed by steam distillation. The organic phase (liquid) is separated off, washed with water, dried and distilled.

Yield: 109 g, m.p. 55° C.

Boiling point: 135–140° C./26 mbar

Example (VII-1)

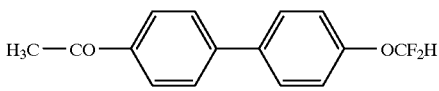

5.3 g (0.025 mol) of 4-acetyl-4'-hydroxybiphenyl are introduced into 35 ml of toluene. 6.7 g (0.075 mol) of 45% strength sodium hydroxide solution are added dropwise to the suspension at 60° C. 0.42 g (0.00125 mol) of tetrabutylphosphonium bromide is subsequently added, and 20 g (0.23 mol) of difluorochloromethane are passed in at 95 to 100° C. in the course of 2 hours. The mixture is cooled, diluted with water and filtered (0.4 g). The toluene phase is separated off, and the aqueous phase is extracted twice using toluene. The combined toluene phases are washed with water, dried and concentrated. This gives 5.9 g (83% of theory) of beige crystals of m.p. 79–81° C.

Example (VIIa-1)

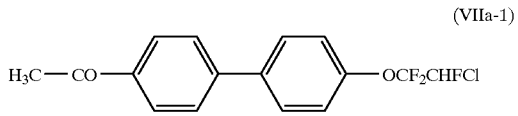

Trifluorochloroethylene is passed at 40° C. into a mixture of 50 g of 4-acetyl-4'-hydroxybiphenyl, 400 ml of acetonitrile, 60 ml of water and 10 g of potassium hydroxide until saturation is reached. The acetonitrile is then removed, and the residue is stirred with 100 ml of water. The solid product is filtered off with suction and dried. The crude product is subsequently stirred with 20 ml of hot cyclohexane and refiltered.

Yield: 45 g

M.p.: 92–94° C.

Example (VIIa-2)

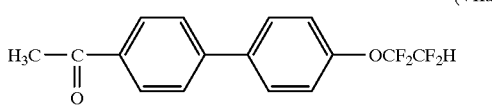

Analogously to Example (VIIa-1), 96 g of 4-acetyl-4'-hydroxybiphenyl and tetrafluoroethylene give 107 g of crude product, which is dissolved in methyl tert-butyl ether and extracted using 300 ml of 5% strength sodium hydroxide solution. The ether phase is concentrated.

Yield: 58 g

M.p.: 95–97° C.

Example (VIIa-3)

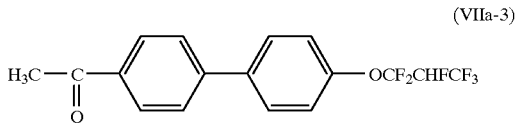

Analogously to Example (VIIa-1), 50 g of 4-acetyl-4'-hydroxybiphenyl and hexafluoropropene gave 59 g of product.

M.p.: 86–87° C.

Example (VIII-1)

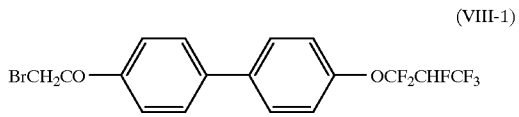

(VIII-1)

29 g (0.08 mol) of 4-hexafluoropropoxyphenylacetophenone of Example (VIIa-3) are suspended in 200 ml of methanol, and 13.4 g (0.084 mol) of bromine are added dropwise at 0° C. Stirring is continued for 12 hours, and the mixture is concentrated. This gives 41.3 g of brown crystals which are purified on silica gel using methylene chloride as the eluent. Yield: 24.6 g (71% of theory) of yellow crystals of m.p. 69–71° C.

The following compounds of the formula (VIII) are obtained analogously and in accordance with the general preparation instructions:

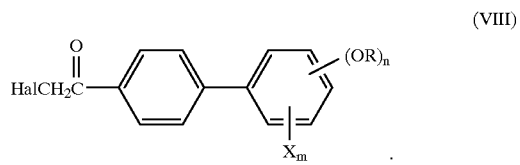

(VIII)

TABLE 2

(m = 0, n = 1)

| Ex. No. | OR | Hal | M.p. [° C.] | Yield (% of theory) |
|---|---|---|---|---|
| VIII-2 | 4-OCHF$_2$ | Br | 83–85 | 62 |
| VIII-3 | 4-OCF$_2$CHFCl | Br | 72–74 | 63 |
| VIII-4 | 4-OCF$_2$CF$_2$H | Br | 56–61° C. | 85 |

Example (VIII-5)

TABLE 2

(m = 0, n = 1)

| Ex. No. | OR | Hal | M.p. [° C.] | Yield (% of theory) |
|---|---|---|---|---|
| VIII-2 | 4-OCHF$_2$ | Br | 83–85 | 62 |
| VIII-3 | 4-OCF$_2$CHFCl | Br | 72–74 | 63 |
| VIII-4 | 4-OCF$_2$CF$_2$H | Br | 56–61° C. | 85 |

7 g (0.0525 mol) of aluminum chloride are suspended in 50 ml of 1,2-dichloroethane. 5.9 g (0.0525 mol) of chloroacetyl chloride are then added dropwise at 5 to 10° C. 13.5 g (0.05 mol) of 4-tetrafluoroethoxybiphenyl, dissolved in 10 ml of dichloroethane, are then added dropwise at –10° C. The mixture is held for a further hour at –10° C., and stirring is then continued for 12 hours at room temperature. The reaction mixture is poured into 150 ml of ice-water, ethyl acetate is added, and the organic phase is separated off. This is washed with bicarbonate solution and then twice with water, dried and concentrated. The crude product is purified over silica gel (eluent methylene chloride). This gives 14.7 g of pale beige crystals (yield 85% of theory) of m.p. 74° C.

Example (X-1)

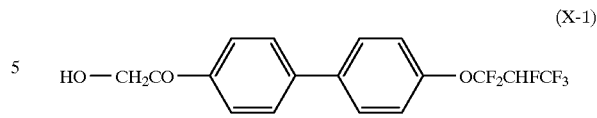

(X-1)

24.3 g (0.055 mol) of bromoketone of Example (VIII-1) are introduced into 145 ml of ethanol/water. 22.5 g (0.33 mol) of sodium formate are added to the suspension, and the mixture is heated at the boil for 12 hours. Some of the ethanol is distilled off, and the mixture is filtered. After washing with water and filtration) the product is dried. 20.7 g (93% of theory) of crystals of m.p. 135° C. are obtained.

The following compounds of the formula (X) are obtained analogously and in accordance with the general preparation instructions:

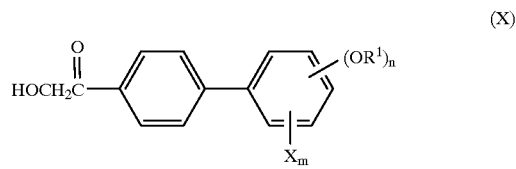

(X)

TABLE 3

(m = 0, n = 1)

| Ex. No. | OR | M.p. [° C.] | Yield [% of theory] |
|---|---|---|---|
| X-2 | 4-OCHF$_2$ | 115–118 | 91 |
| X-3 | 4-OCF$_2$CHFCl | 160 | 97 |
| X-4 | 4-OCF$_2$CF$_2$H | 155–160 | 90 |

Example (XI-1)

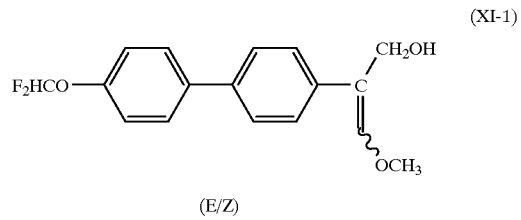

(XI-1)

(E/Z)

5 g (0.018 mol) of 4-difluoromethoxyphenyl-ω-hydroxyacetophenone of Example (X-2) are dissolved in 50 ml of 1,2-dimethoxyethane, and 5 ml of water are added. 1.85 g (0.0225 mol) of sodium acetate and 1.9 g (0.0225 mol) of 0-methylhydroxylamine hydrochloride are subsequently added, and the mixture is stirred overnight at room temperature. The reaction mixture is poured into 180 ml of ice-water and filtered off with suction, and the product is washed with water and dried. This gives 5.4 g of pale beige crystals of m.p. 65–81° C. (E/Z mixture: 43/57).

The following compounds of the formula (XI) are obtained analogously and in accordance with the general preparation instructions:

(XI)

$$\text{HOCH}_2\text{C}(=\text{N-OCH}_3)-\text{C}_6\text{H}_4-\text{C}_6\text{H}_3(\text{OR}^1)_n(X_m)$$

TABLE 4

(m = 0, n = 1)

| Ex. No. | OR | M.p. [° C.] | Yield (% of theory) |
|---|---|---|---|
| XI-2 | 4-OCHF₂CHFCl | *) | 89 |
| XI-3 | 4-OCF₂CHF₂ | *) | 83 |
| XI-4 | 4-OCF₂CHFCF₃ | *) | 82 |

*) Since the melting range of the resulting E/Z mixtures is very broad, the melting point is not a characteristic value.

Example (XIII-1)

(XIII-1)

$$F_2\text{HCO}-\text{C}_6\text{H}_4-\text{C}_6\text{H}_4-\text{CH}(\text{NH}_2\cdot\text{HCl})-\text{CH}_2\text{OH}$$

9.2 g (0.2425 mol) of sodium boranate are introduced into 250 ml of absolute THF, and 27.6 g (0.2425 mol) of trifluoroacetic acid in 25 ml of THF are then added dropwise at 20° C. in the course of 10 minutes. 14.9 g (0.0485 mol) of the oxime ethers of Example (XI-1), dissolved in 25 ml of THF, are subsequently added dropwise to the cloudy, colorless reaction mixture at 15° C. in the course of 15 minutes. The mixture is stirred for 2 hours at room temperature, and stirring is then continued for 2 hours at boiling point. After cooling, 150 ml of water are carefully added at approximately 10° C., and stirring is continued for 12 hours at room temperature. The mixture is filtered, and the filtrate is concentrated. After stirring with 2N HCl, the white crystals are filtered off with suction, washed with methylene chloride and dried.

This gives 13 g of white crystals of m.p. 180° C. (decomp.)

Yield: 82% of theory.

Example (XIII-2)

The compound of the formula (XIII-2)

$$\text{CClFHCF}_2-\text{O}-\text{C}_6\text{H}_4-\text{C}_6\text{H}_4-\text{CH}(\text{NH}_2\cdot\text{HCl})-\text{CH}_2\text{OH}$$

of m.p. 197° C. (decomposition) is obtained analogously to Example (XIII-1).

Yield: 91% of theory.

Example (XIII-3)

The compound of the formula (XIII-3)

$$\text{HF}_2\text{CCF}_2-\text{O}-\text{C}_6\text{H}_4-\text{C}_6\text{H}_4-\text{CH}(\text{NH}_2\cdot\text{HCl})-\text{CH}_2\text{OH}$$

of m.p. 250° C. (decomposition) is obtained analogously to Example (XIII-1).

Yield: 53% of theory.

Example (XIV-1)

(XIV-1)

$$2,6\text{-F}_2\text{-C}_6\text{H}_3-\text{CO}-\text{NH}-\text{CH}(\text{CH}_2\text{OH})-\text{C}_6\text{H}_4-\text{C}_6\text{H}_4-\text{OCHF}_2$$

1.52 g (0.0086 mol) of 2,6-difluorobenzoyl chloride are added dropwise (at 10 to 20° C.) to a mixture of 2.5 g (0.0086 mol) of 2-amino-2-phenyl-(4-difluoromethoxy phenyl)-ethanol of Example (XIII-1) and 0.9 g (0.009 mol) of triethylamine in 50 ml of THF. The mixture is subsequently stirred for 3 hours and concentrated, the product is taken up in methylene chloride, the mixture is washed three times with water, dried and reconcentrated.

This gives 3.3 g of pale beige crystals of m.p. 146° C.

Yield: 83.5% of theory.

The following compounds of the formula (XIV) are obtained analogously and in accordance with the general preparation instructions:

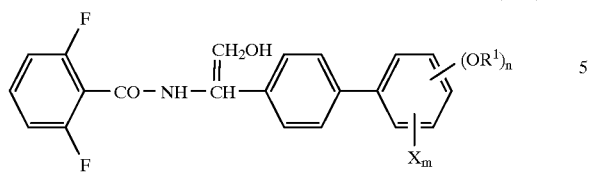

(XIV)

TABLE 5

| | (m = 0, n = 1) | | |
|---|---|---|---|
| Ex. No. | OR | M.p. [° C.] | Yield [% of theory] |
| XIV-2 | 4-OCF$_2$CHFCl | 194–195 | 54 |
| XIV-3 | 4-OCF$_2$CHFCF$_3$ | 142–145 | 73 |
| XIV-4 | 4-OCF$_2$CF$_2$H | 184–186 | 81 |

Example (XVII-1)

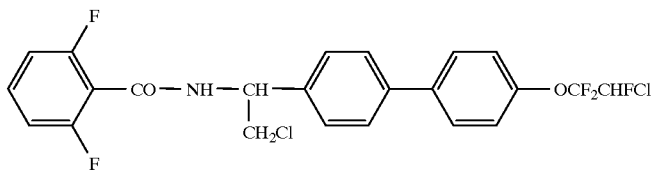

(XVII-1)

10.6 g (0.022 mol) of hydroxyethylamide of Example (XIV-2) are suspended in 100 ml of dry toluene. 10.5 g (0.088 mol) of thionyl chloride are added dropwise without cooling, a clear yellow solution being formed. This is heated to 70° C. and held at this temperature for 2 hours. After cooling to 0° C., the mixture is filtered, and the product is washed with a small amount of toluene and dried.

This gives 8.8 g (79% of theory) of white crystals of m.p. 190–192° C.

Example (XVII-2)

Analogously to Example XVII-1

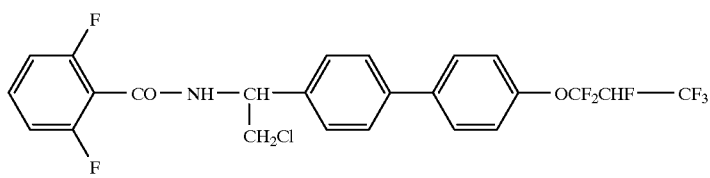

(XVII-2)

white crystals of m.p. 161–164° C. (83% of theory) are obtained.

Example (XVII-3)

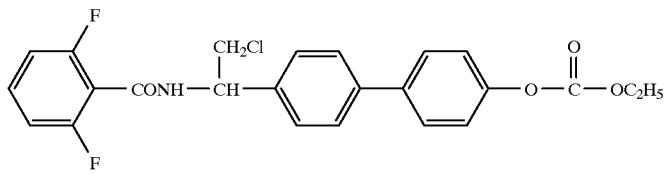

130.4 g (0.98 mol) of aluminum chloride are introduced in portions at 5° C. in the course of 30 minutes into a mixture of 53 g (0.213 mol) of 2-(2,6-difluorobenzoylamido)-2-methoxy-1-chloroethane, 48.4 g (0.2 mol) of 4-ethoxycarbonyloxybiphenyl and 12 ml of glacial acetic acid in 200 ml of methylene chloride. In the course of this, the color of the batch changes via blue to a reddish violet. The reaction mixture is stirred for 1 hour at 5° C. and for 1 hour at 10° C. and carefully poured onto ice, the suspension is carefully decanted off from water and concentrated on a rotary evaporator, the residue is treated with 50 ml of acetonitrile, and the crystals which have precipitated are filtered off with suction. Yield 42.8 g (47% of theory), m.p. 209° C.

The following compounds of the formula (XVII)

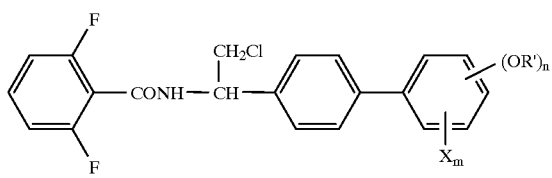

(XVII)

are obtained analogously or in accordance with the general information on the preparation:

TABLE 6

| | (m = 0, n = 1) | |
|---|---|---|
| Ex. No. | OR' | M.p. [° C.] |
| (XVII-4) | 4-OC—C(CH₃)₃<br>‖<br>O | 125–130 |
| (XVII-5) | 4-OC—CH₃<br>‖<br>O | 225–130 |

Example for the use of the compound of Example (I-8)

First, 0.22 ml (0.005 mol) of 45% NaOH solution and then, at 0° C., 0.5 g (0.005 mol) of ethyl bromide are added dropwise to 1.75 g of the compound of Example (I-8) in 10 ml of dimethylformamide. The mixture is stirred for 2 hours at room temperature and poured into 50 ml of ice-water, and the crystals are filtered off with suction. The filtrate is extracted using ethyl acetate, and the ethyl acetate phase is dried and concentrated in vacuo. The crystals are combined, stirred with 20 ml of diisopropyl ester and filtered off with suction. Yield 1.1 g (58% of theory), m.p. 148 to 150° C.

In the use examples which follow, the compound of the formula (A)

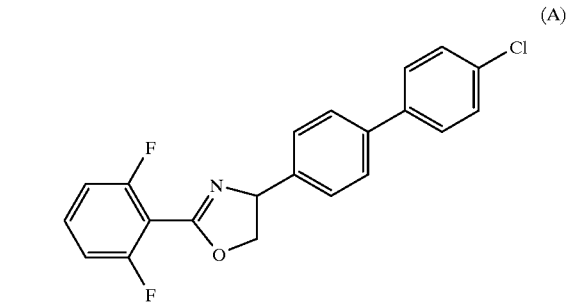

(A)

which is known from EP-A-0 432 661 was employed as comparison substance.

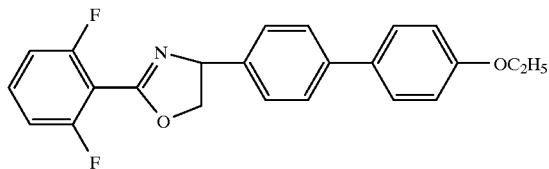

Ex. 142 in EP-0 432 661

USE EXAMPLES

Example A

Plutella test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the diamond-back moth (*Plutella maculipennis*) while the leaves are still moist.

After the specified periods of time, the destruction in % is determined. 100% means that all the caterpillars have been killed; 0% means that none of the caterpillars have been killed.

In this test, a destruction rate of 100% was caused, after 3 days, for example by the compound of Preparation Example (I-2) at an exemplary active compound concentration of 0.01% and a destruction rate of 100% was caused, after 7 days, by the compound of Preparation Example I-11 at an exemplary active compound concentration of 0.1%.

Example B

Spodoptera test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of active compound of the desired concentration and are infested with caterpillars of the fall armyworm (*Spodoptera frugiperda*) while the leaves are still moist.

After the specified periods of time, the destruction in % is determined. 100% means that all the caterpillars have been killed; 0% means that none of the caterpillars have been killed.

In this test, a destruction rate of 100% was achieved, after 7 days, for example by the compound of Preparation Example (I-11) at an exemplary active compound concentration of 0.1%.

Example C

Tetranychus test (OP resistant/spray treatment)
Solvent: 3 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (*Phaseolus vulgaris*) which are severely infested with all stages of the greenhouse red spider mite (*Tetranychus urticae*) are sprayed with an active compound preparation of the desired concentration.

After the specified periods of time, the destruction in % is determined. 100% means that all the spider mites have been killed; 0% means that none of the spider mites have been killed.

In this test, a destruction rate of 95% was achieved, after 14 days, for example by the compound of Preparation Example (I-2) at an exemplary active compound concentration of 0.000032%, while the known compound (A) only caused a destruction rate of 80%.

Example D

Ecdysis test on polyphagous tick nymphs
Test animals: *Amblyomma variegatum*, nymphal stages which have sucked themselves full
Solvent: 35 parts by weight of ethylene glycol monomethyl ether
Emulsifier: 35 parts by weight of nonylphenol polyglycol ether To produce a suitable formulation, 3 parts by weight of active compound are mixed with 7 parts of the abovementioned solvent-emulsifier mixture, and the resulting emulsion concentrate is diluted with water to the concentration desired in each case.

10 nymphs which have sucked themselves full are immersed for 1 minute into the preparation of active compound to be tested. The animals are transferred to Petri dishes (Θ9.5 cm) which are equipped with filter paper disks and covered. After the nymphs have remained in a control-environment cabinet for 5–6 weeks, the ecdysis rate is determined.

100% means that all the animals have undergone normal ecdysis; 0% means that none of the animals has undergone normal ecdysis.

In this test, an ecdysis rate of 0% was shown, for example, by the compound of Preparation Example (I-2) at an exemplary active compound concentration of 1000 ppm.

Example E

Blowfly larvae test/development-inhibitory action
Test animals: *Lucilia cuprina* larvae
Solvent: 35 parts by weight of ethylene glycol monomethyl ether
Emulsifier: 35 parts by weight of nonylphenol polyglycol ether To produce a suitable formulation, 3 parts by weight of active compound are mixed with 7 parts of the abovementioned solvent-emulsifier mixture, and the resulting emulsion concentrate is diluted with water to the concentration desired in each case.

Approximately 20 *Lucilia cuprina* larvae are introduced into a test tube which contains approximately 1 cm$^3$ of horse meat and 0.5 ml of the preparation of active compound to be tested. After 24 and 48 hours, the effectiveness of the preparation of active compound is determined. The test tubes are transferred into beakers whose bottom is covered with sand. After a further 2 days, the test tubes are removed, and the pupae are counted.

The activity of the preparation of the active compound is assessed taking into account the number of flies which have emerged after 1.5 times the development time and an untreated control. 100% means that no flies have emerged; 0% means that all flies have emerged normally.

In this test, an activity of 100% was shown, for example, by the compound of Preparation Example I-2 at an exemplary active compound concentration of 1000 ppm.

Example F

Nephotettix test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Rice seedlings (*Oryza sativa*) are treated by being dipped into the preparation of active compound of the desired concentration and are infested with the green rice leafhopper (*Nephotettix cincticeps*) while the seedlings are still moist.

After the specified period of time, the destruction in % is determined. 100% means that all the leafhoppers have been killed; 0% means that none of the leafhoppers have been killed.

In this test, a destruction rate of at least 90% was caused, after 6 days, for example by the compounds of Preparation Examples I-7, I-8 and I-11 at an exemplary active compound concentration of 0.1%.

It will be understood that the specification and examples are illustrative but not limitive of the present invention and that other embodiments within the spirit and scope of the invention will suggest themselves to those skilled in the art.

We claim:

1. A compound of the formula (Ib)

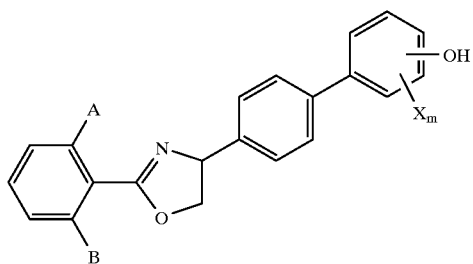

in which

A represents hydrogen, fluoro or chloro,

B represents fluoro or chloro x represents halogen, $C_1$–$C_5$-alkyl or $C_1$–$C_6$-alkoxy m represents 0, 1 or 2.

2. a compound according to claim 1 in which

A represents hydrogen, fluoro or chloro,

B represents fluoro or chloro x represents fluorine, chlorine or bromine m represents 0 or 1.

3. A compound

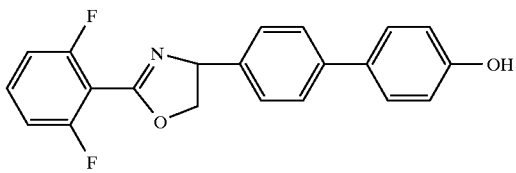

* * * * *